(12) United States Patent
Chana et al.

(10) Patent No.: US 10,585,057 B2
(45) Date of Patent: Mar. 10, 2020

(54) DETECTING COMPOSITION OF A SAMPLE BASED ON THERMAL PROPERTIES

(71) Applicant: OXFORD UNIVERSITY INNOVATION LIMITED, Botley, Oxford (GB)

(72) Inventors: Kamaljit Singh Chana, Oxford (GB); Jonathan Shamus Sullivan, Fleet (GB)

(73) Assignee: OXFORD UNIVERSITY INNOVATION LIMITED, Botley, Oxford (GB)

( * ) Notice: Subject to any disclaimer, the term of this patent is extended or adjusted under 35 U.S.C. 154(b) by 237 days.

(21) Appl. No.: 15/536,291

(22) PCT Filed: Dec. 16, 2015

(86) PCT No.: PCT/GB2015/054033
§ 371 (c)(1),
(2) Date: Jun. 15, 2017

(87) PCT Pub. No.: WO2016/097723
PCT Pub. Date: Jun. 23, 2016

(65) Prior Publication Data
US 2017/0350841 A1    Dec. 7, 2017

(30) Foreign Application Priority Data
Dec. 16, 2014   (GB) .................................. 1422370.5

(51) Int. Cl.
*G01K 17/00*   (2006.01)
*G01K 1/00*    (2006.01)
(Continued)

(52) U.S. Cl.
CPC ............. *G01N 27/18* (2013.01); *G01N 25/00* (2013.01); *G01N 25/18* (2013.01); *G01N 25/482* (2013.01);
(Continued)

(58) Field of Classification Search
USPC ................... 374/29, 144, 208, 166, 148, 45
See application file for complete search history.

(56) References Cited

U.S. PATENT DOCUMENTS 4,220,041 A   9/1980 Potter
4,869,596 A   9/1989 Klein et al.
(Continued)

FOREIGN PATENT DOCUMENTS

CN   101776628 A   7/2010
EP   0208096 A1    1/1987
(Continued)

OTHER PUBLICATIONS

B J Bellhouse and F H Bellhouse. "Thin-film gauges for the measurement of velocity or skin friction in air, water or blood." Journal of Scientific Instruments (Journal of Physics E). Series 2. vol. 1. Received Apr. 8, 1968. pp. 1211-1213.
(Continued)

*Primary Examiner* — Mirellys Jagan
(74) *Attorney, Agent, or Firm* — Harness, Dickey & Pierce, P.L.C.

(57) ABSTRACT

The invention relates to detecting a composition of a sample or contamination in liquids by detecting corresponding changes in their thermal properties. In a disclosed arrangement, an apparatus is provided comprising a first probe element configured to provide a first surface in direct contact with the sample and a second surface that is not in direct contact with the sample. A measurement system measures a rate of heat transfer through the first surface. A processing unit analyses the measured rate of heat transfer in order to detect a heat transfer characteristic of the sample that is indicative of a composition of the sample.

20 Claims, 11 Drawing Sheets

(51) Int. Cl.
| | |
|---|---|
| G01K 13/00 | (2006.01) |
| G01K 7/00 | (2006.01) |
| G01N 25/00 | (2006.01) |
| G01N 27/18 | (2006.01) |
| G01N 33/28 | (2006.01) |
| G01N 25/18 | (2006.01) |
| G01N 25/48 | (2006.01) |
| G01N 25/08 | (2006.01) |

(52) U.S. Cl.
CPC ..... *G01N 33/2847* (2013.01); *G01N 33/2858* (2013.01); *G01N 25/08* (2013.01)

(56) References Cited

U.S. PATENT DOCUMENTS

| | | | |
|---|---|---|---|
| 5,044,767 A | 9/1991 | Gustafsson | |
| 5,330,268 A | 7/1994 | Klein et al. | |
| 5,795,064 A | 8/1998 | Mathis | |
| 6,095,680 A * | 8/2000 | Baratta | G01N 25/18 374/12 |
| 6,308,564 B1 | 10/2001 | Wehrmeyer et al. | |
| 6,676,287 B1 | 1/2004 | Mathis et al. | |
| 7,048,436 B2 | 5/2006 | Mathis | |
| 7,398,680 B2 * | 7/2008 | Glasbergen | E21B 47/1005 374/136 |
| 9,017,258 B2 | 4/2015 | Ollmar et al. | |
| 9,636,035 B2 | 5/2017 | Ollmar et al. | |
| 2004/0165645 A1 | 8/2004 | Mathis | |
| 2005/0105583 A1 | 5/2005 | Xiao et al. | |
| 2007/0127543 A1 | 6/2007 | Petrovic | |
| 2008/0298426 A1 * | 12/2008 | Koschack | F23J 3/02 374/7 |
| 2010/0204928 A1 | 8/2010 | Lepsch et al. | |
| 2014/0177673 A1 | 6/2014 | Bliss et al. | |
| 2014/0369379 A1 | 12/2014 | Emanuel et al. | |

FOREIGN PATENT DOCUMENTS

| | | |
|---|---|---|
| EP | 0280229 A2 | 8/1988 |
| EP | 0406282 B1 | 10/1993 |
| EP | 2391268 A2 | 12/2011 |
| EP | 2494331 A1 | 9/2012 |
| JP | S59-042441 A | 3/1984 |
| JP | H034256 U | 1/1991 |
| JP | 2001174424 A | 6/2001 |
| JP | 2014/130075 A | 7/2014 |
| KR | 20050080968 A | 8/2005 |
| WO | WO-2000070333 A1 | 11/2000 |
| WO | WO-03002998 A2 | 1/2003 |
| WO | WO-03002998 A3 | 8/2003 |
| WO | WO-2006063427 A1 | 6/2006 |
| WO | WO-2010086326 A2 | 8/2010 |
| WO | WO-2011065877 A1 | 6/2011 |
| WO | WO-2012-131281 A1 | 10/2012 |

OTHER PUBLICATIONS

Tapomayukh Battacharjee et al. "Material Recognition from Heat Transfer given Varying Initial Conditions and Short-Duration Contact." Healthcare Robotics Lab, Institute for Robotics and Intelligent Machines, Georgia Institute of Technology, Atlanta, GA 30308. Jul. 2015.

Mark F. Fleszar. "Thermal Effusivity As a Non-Destructive Method to Characterize Thin Films." Technical Report ARCCB-TR-03014. US Army Armament Research, Development and Engineering Center, Close Combat Armaments Center, Benét Laboratories, Watervliet, NY 12189-4000. Nov. 2003.

Mohamed K. Ghorab et al. "Application of Thermal Effusivity as a Process Analytical Technology Tool for Monitoring and Control of the Roller Compaction Process." AAPS PharmSciTech; 8(1) Article 23. Published Mar. 23, 2007.

Silas E. Gustafsson. "Transient Hot Strip Techniques for Measuring Thermal Conductivity and Thermal Diffusivity." The Rigaku Journal, vol. 4, No. 1 & 2. Dec. 1987.

Silas E. Gustafsson. "Transient plane source techniques for thermal conductivity and thermal diffusivity measurements of solid materials." Rev. Sci. Instrum. 62(3). Mar. 1991. American Institute of Physics.

M. Gustavsson et al. "Thermal effusivity measurements of insulating liquids using microsized hot strip probes." Review of Scientific Instruments. vol. 74, No. 10. Oct. 2003. American Institute of Physics.

Adam Harris et al. "Measuring the thermal conductivity of heat transfer fluids via the modified transient plane source (MTPS)." J Therm Anal Calorim. Published Online May 6, 2014.

T. Log and S. E. Gustafsson. "Transient Plane Source (TPS) Technique for Measuring Thermal Transport Properties of Building Materials." Fire and Materials, vol. 19, Issue 1. Jan./Feb. 1995.

Ligi Mathews et al. "Monitoring Blend Uniformity with Effusivity." Pharmaceutical Technology. Apr. 2002.

Nancy Mathis. "Transient thermal conductivity measurements: comparison of destructive and nondestructive techniques." High Temperatures—High Pressures, vol. 32. pp. 321-327. Jan. 2000. Presented at the 15th European Conference on Thermophysical Properties, Würzburg, Germany, Sep. 5-9, 1999.

L. Salmi. "Hot Disk Medical® A deeper understanding." Scientific discussions. Feb. 24, 2010.

A Sizov et al. "Thermal conductivity versus depth profiling of inhomogeneous materials using the hot disc technique." Review of Scientific Instruments. vol. 87, Issue 7. Jul. 2016.

Jumpei Uchiyama et al. "Evaluation of risk and benefit in thermal effusivity sensor for monitoring lubrication process in pharmaceutical product manufacturing." Drug Development and Industrial Pharmacy. Published online May 21, 2013.

Jennie Sköld. "Detection of Damage in the Equine Hoof. A possible new application for the Hot Disk Method?" Master's thesis in Engineering Physics. Department of Physics. Division of Condensed Matter Physics. Chalmers University of Technology. Gothenburg, Sweden. Feb. 17, 2017.

Josef Mizzi, "The Design of a Brushless drive to be operated with a Stirling Engine", Dissertation. University of Malta, Apr. 2014.

Jean Maulard, "Calibration Method Used at Onera for Hotshot and Shock Tube Heat Transfer Transducers", Proc. 3rd International Congress on Instrumentation in Aerospace Simulation Facilities. IEEE/G-AES. May 1969, pp. 96-106.

Leonard Bogdan, "High-Temperature, Thin-Film Resistance Thermometers for Heat Transfer Measurement", NASA, CR-26, 1964.

* cited by examiner

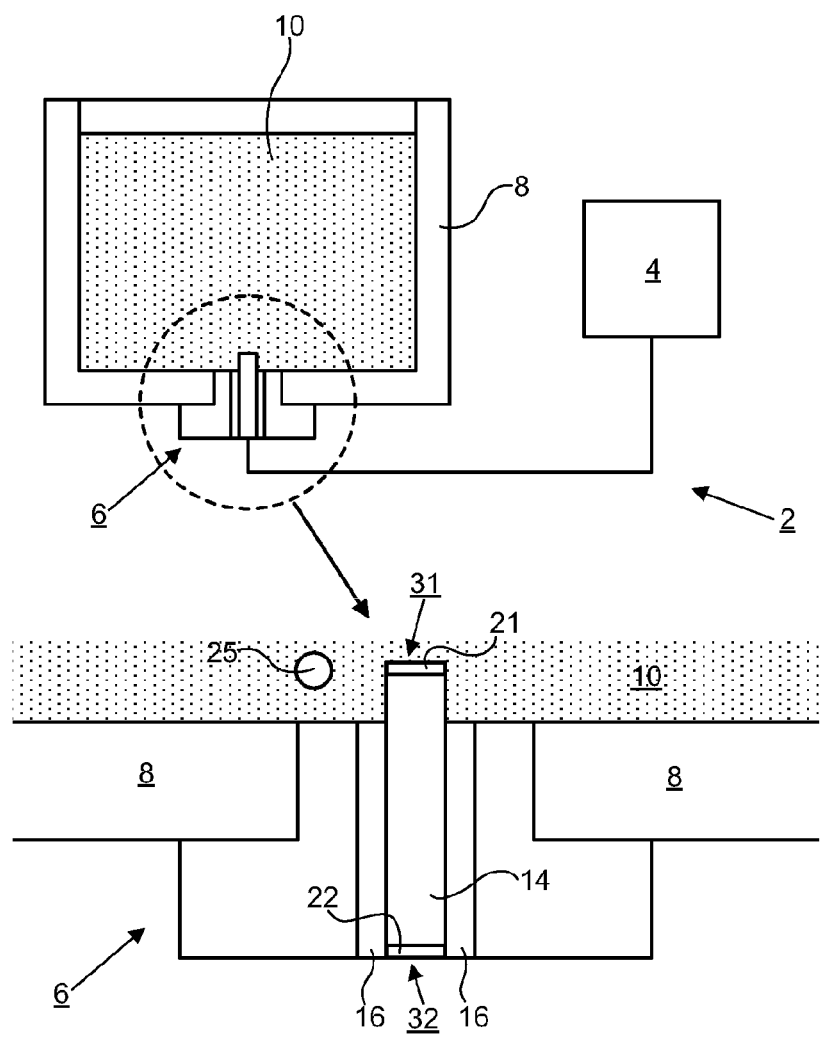

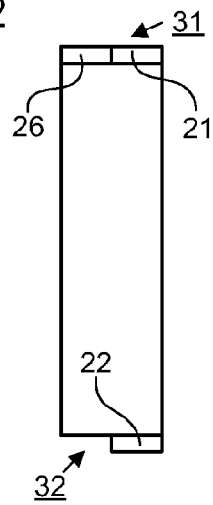
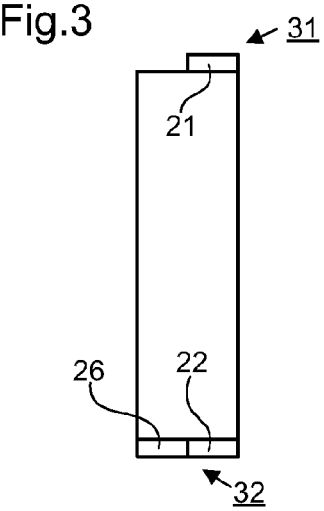
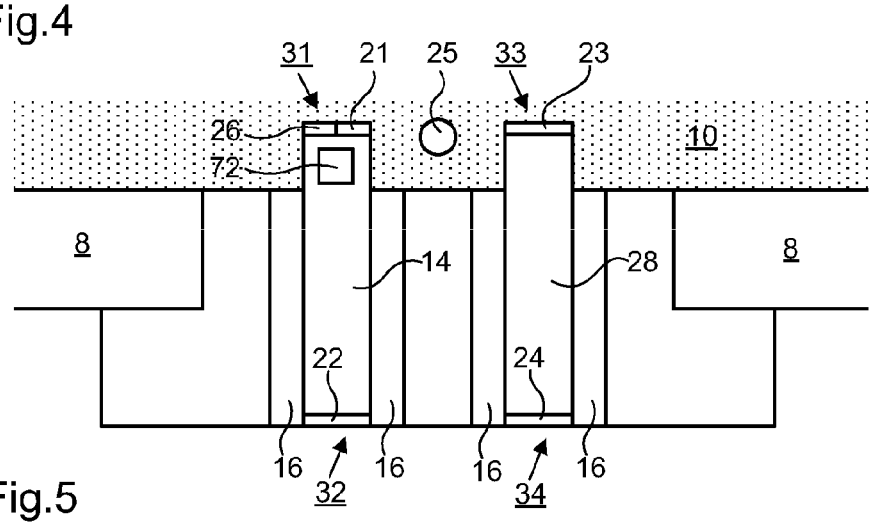
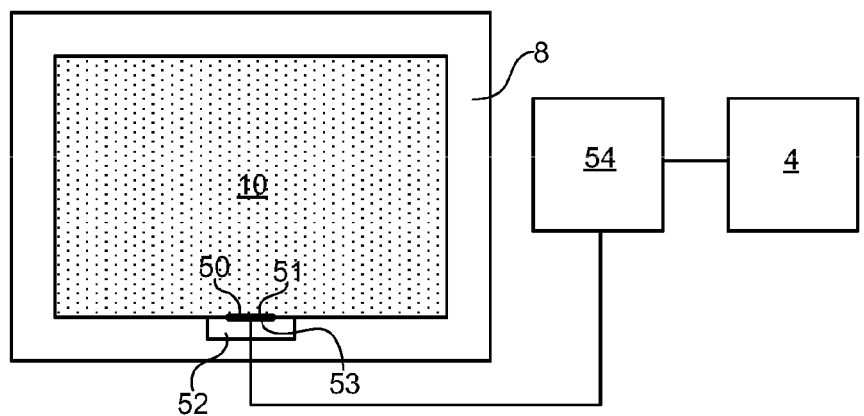

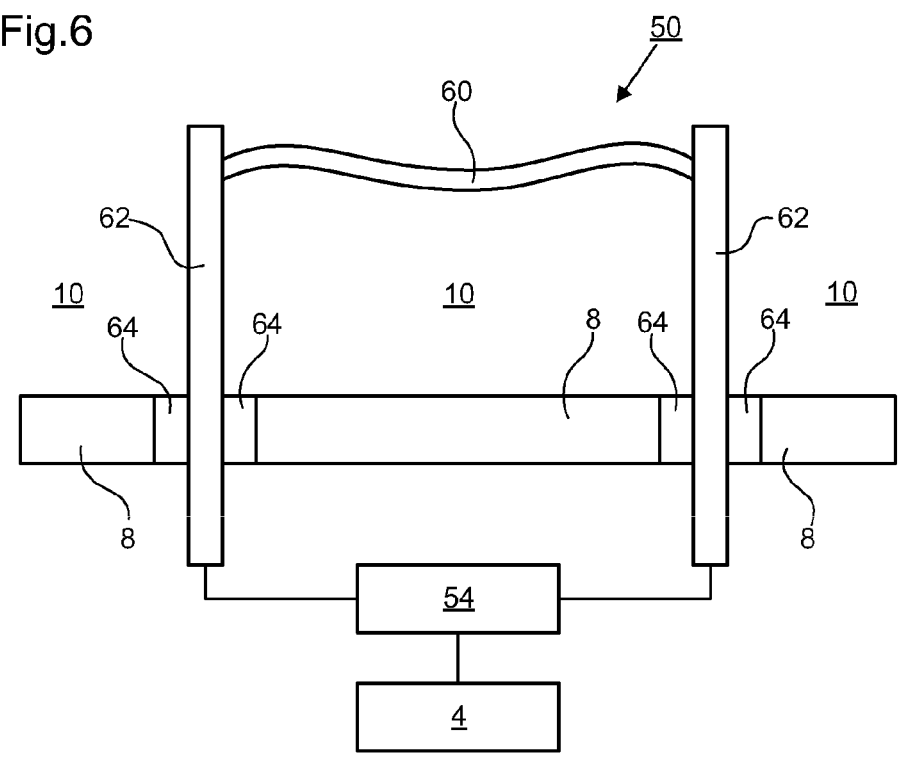

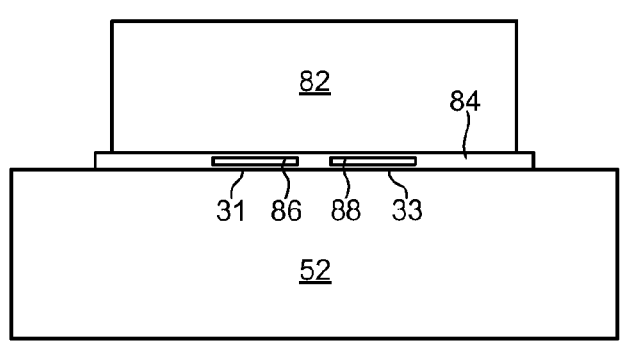
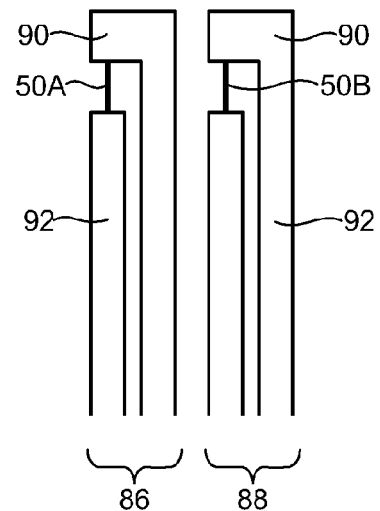
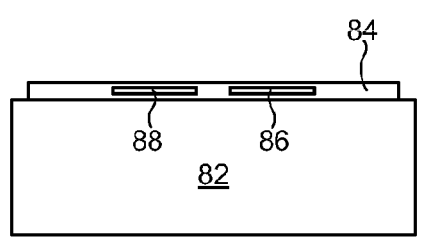
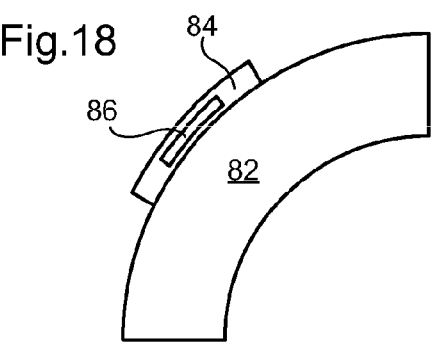

DETECTING COMPOSITION OF A SAMPLE BASED ON THERMAL PROPERTIES

CROSS REFERENCE TO RELATED APPLICATIONS

This application is a U.S. National Phase Application under 35 U.S.C. 371 of International Application No. PCT/GB2015/054033 filed on Dec. 16, 2015 and published in Japanese as WO 2016/097723 A1 on Jun. 23, 2016. This application claims priority to British Application No. 1422370.5 filed on Dec. 16, 2014. The entire disclosures of all of the above applications are incorporated herein by reference.

The invention relates to detecting a composition of a sample based on thermal properties of the sample. The invention relates particularly to detection of contamination in liquids by detecting corresponding changes in their thermal properties. The invention is applicable in particular to detecting levels and types of contamination in lubricating and cooling oils, hydraulic fluid and fuel, in apparatus such as engines and gearboxes. The invention is also applicable to detecting contamination in cleaning liquids used in food manufacturing facilities. The invention is also applicable to detecting the composition of samples which are not liquids, such as solids or gels or multiphase materials. The invention is applicable to detecting variations in chemical composition and structural composition.

Liquids such as lubricating and cooling oils, hydraulic fluid and fuel are regularly required to be replaced/filtered as they degrade or become contaminated, in order to avoid unnecessary damage to machines that rely on the liquids. Degradation can occur via oxidation due to exposure to high temperature, the addition of debris (metallic or non-metallic) or another fluid and/or aging of the fluid.

Continuous oil condition monitoring of machinery and lubricant testing is fast becoming the established method of predicting and avoiding impending machinery breakdown. Oil monitoring can in principle be performed off-line, online and in-line. In off-line monitoring a sample of the liquid may be taken and sent to a laboratory for analysis. Sophisticated analyses can be performing off-line but there is an inevitable delay in obtaining the results; they are not available in "real time". In an on-line monitoring system samples may be taken from the oil system and analysed immediately in a device forming part of the machinery being monitoring. The flow rate can be affected by the sampling process if the sample size is relatively large but such systems can provide real time monitoring. In-line monitoring can be difficult to implement and can influence the system, but again offers real time monitoring.

Real time sensors that operate based on monitoring the dielectric constant of a liquid are known. The dielectric constant is a measure of the ability of a fluid to resist an electrical field. These sensors work well in detecting water contamination as oil and water have very different dielectric values. However, a major drawback is that they are temperature dependant. Other known sensors operate based on various optical techniques, such as infrared spectrometry or particle sizing. Inductive coil magnetometry systems have also been deployed where ferrous and non-ferrous particles are identified and quantified. This approach is advantageous in that it makes it possible to track the progress of debris contamination. In-line X-ray fluorescence spectroscopy is being developed for use in sensors. Capacitive sensors have also been developed where water saturation can be detected.

Detection of the composition of samples which are not liquids can require expensive, time-consuming and/or destructive analysis techniques. For example, X-rays can be used to analyse the internal structure of objects. However, X-ray equipment can be expensive and bulky. Objects can be broken up to see the internal structure but this may involve irreversible damage to the object. Objects having a complex chemical structure may be broken up and chemical analysis techniques may be used to determine the chemical composition. However, the breaking up may damage the object and the chemical analyses may take considerable time and expensive to perform.

It is desirable to provide an alternative, improved and/or simpler way of detecting a composition of a sample and/or of monitoring liquid quality in real time.

The scope of the invention is defined in the appended claims.

According to an aspect of the invention, there is provided an apparatus for detecting a composition of a sample, comprising: a first probe element configured to provide a first surface in direct contact with the sample and a second surface that is not in direct contact with the sample; a measurement system configured to measure a rate of heat transfer through the first surface; and a processing unit configured to analyse the measured rate of heat transfer in order to detect a heat transfer characteristic of the sample that is indicative of a composition of the sample.

The apparatus enables sensitive detection of a composition of a sample, optionally in real time and using a mechanically simple and reliable construction. The approach intrinsically deals with variations in the temperature of the sample. Such variations in temperature will not have a significant negative impact on measurement accuracy, in contrast to prior art methods based on other principles. The apparatus may be adapted to detect the composition of any phase of matter, including solids, liquids, gases, gels and mixtures of any of these phases or other phases. In an embodiment the apparatus is capable of detecting a chemical composition of a sample and/or comparing the chemical composition of one sample with the chemical composition of another sample. The apparatus may be used for quality control purposes by detecting differences in chemical composition between nominally identical objects. In an embodiment the apparatus is capable of detected a structural composition of a sample and/or comparing the structural composition of one sample with the structural composition of another sample. For example the apparatus may be arranged to detect unwanted defects, inclusions or voids in a manufactured object, such as an object formed from a cast. The apparatus may be used for quality control purposes by detecting differences in structural composition between nominally identical manufactured objects.

In an embodiment there is provided an apparatus for detecting contamination of a liquid, comprising: a first probe element configured to provide a first surface in direct contact with the liquid and a second surface that is not in direct contact with the liquid; a measurement system configured to measure a rate of heat transfer through the first surface; and a processing unit configured to analyse the measured rate of heat transfer in order to detect a change in a heat transfer characteristic of the liquid that is indicative of contamination of the liquid.

The apparatus enables sensitive detection of contamination in a liquid in real time using a mechanically simple and reliable construction. The approach intrinsically deals with variations in the temperature of the liquid. Such variations in temperature will not have a significant negative impact on measurement accuracy, in contrast to prior art methods based on other principles.

In an embodiment the first probe element can be heated to improve measurement accuracy. For example, the heating can increase a temperature difference between the sample (e.g. liquid) and the probe element, which can increase accuracy.

In an embodiment multiple (e.g. two) probe elements are provided. Providing multiple probe elements may improve measurement accuracy by provided multiple independent measurements of the heat transfer characteristics of the sample (e.g. liquid). Alternatively or additionally, different probe elements may be heated or cooled by different amounts and/or be formed from materials with different conductivities in order to cause the rate of heat transfer from the sample (e.g. liquid) to the probe element to be different for different probe elements. In this scenario combining the measurements from the different probe elements may make it possible to obtain the heat characteristics of the sample (e.g. liquid) without measuring the temperature of the sample (e.g. liquid). This may improve the simplicity of operation and/or construction, improve reliability and/or longevity, and/or reduce manufacturing costs.

According to another aspect, there is provided an apparatus for detecting a composition of a sample, comprising: one or more resistive elements, each resistive element configured to be in thermal contact with a sample; a measurement system configured to 1) drive an electrical current through each of the one or more resistive elements in order to supply heating at each of the one or more resistive elements, and 2) measure a change in a resistance of each of the one or more resistive elements; and a processing unit configured to analyse a relationship between the amount of heat supplied to the each of the one or more resistive elements and the change in the resistance of each of the one or more resistive elements in order to detect a heat transfer characteristic of the sample that is indicative of a composition of the sample.

In an embodiment, there is provided an apparatus for detecting contamination of a liquid, comprising: a resistive element configured to be in direct contact with the liquid; a measurement system configured to 1) drive an electrical current through the resistive element in order to supply heating at the resistive element, and 2) measure a change in resistance of the resistive element; and a processing unit configured to analyse a relationship between the amount of heat supplied to the resistive element and the change in the resistance of the resistive element in order to detect a change in a heat transfer characteristic of the liquid that is indicative of contamination of the liquid.

According to this aspect the portion of the apparatus that is in contact with the sample (e.g. liquid) can be particularly simple, thereby favouring low cost and high reliability.

In an embodiment the resistive element is mounted on a substrate in such a way that at least 10% of the surface area of the resistive element is in contact with the substrate (e.g. as a thin film element mounted on a substrate). An advantage of this arrangement is that significant heating power can be applied to the resistive element without the resistive element reaching temperatures which are high enough to potentially damage the sample (e.g. liquid) being monitored. The substrate acts to conduct heat effectively away from the resistive element.

In an alternative embodiment the resistive element is mounted so as to be in direct contact with the sample (e.g. liquid) over more than 90% of the surface area of the resistive element. An advantage of this arrangement is that the temperature of the resistive element can be varied quickly, thereby allowing pyrolytic cleaning and/or rapid formation of vapour phases (which can be used to detect certain contaminants, such as water).

According to another aspect, there is provided a method of detecting a composition of a sample, comprising: providing a first probe element having a first surface in direct contact with the sample and a second surface that is not in direct contact with the sample; measuring a rate of heat transfer through the first surface; and analysing the measured rate of heat transfer in order to detect a heat transfer characteristic of the sample that is indicative of a composition of the sample.

In an embodiment there is provided a method of detecting contamination of a liquid, comprising: providing a first probe element having a first surface in direct contact with the liquid and a second surface that is not in direct contact with the liquid; measuring a rate of heat transfer through the first surface; and analysing the measured rate of heat transfer in order to detect a change in a heat transfer characteristic of the liquid that is indicative of contamination of the liquid.

In an embodiment, the rate of heat transfer through the first surface is measured at a temperature at the first surface that is below the boiling point of a predetermined contaminant and at a temperature at the first surface that is above the boiling point of the predetermined contaminant; and the detection of a change in the heat transfer characteristic comprises comparing the measured rate of heat transfer at the temperature at the first surface that is below the boiling point of the predetermined contaminant with the measured rate of heat transfer at the temperature at the first surface that is above the boiling point of the predetermined contaminant. It is expected that the heat transfer characteristics of the sample (e.g. liquid) will depend sensitively on whether the predetermined contaminant is present. By heating the first surface above the boiling point of the predetermined contaminant the amount of the predetermined contaminant present, if any, near the first surface will be greatly reduced. If there is a significant amount of the predetermined contaminant in the sample (e.g. liquid) we should expect a large difference in heat transfer characteristics between the measurements carried out below and above the boiling point of the predetermined contaminant. This method therefore provides a sensitive way of detecting the presence and/or amount of predetermined contaminants.

According to another aspect, there is provided a method of detecting a composition of a sample, comprising: providing one or more resistive elements, each in thermal contact with a sample; heating each of the one or more resistive elements by driving an electrical current through the resistive element; measuring a change in resistive of each of the one or more resistive elements; analysing a relationship between the amount of heat supplied to the each of the one or more resistive elements and the change in the resistance of each of the one or more resistive elements in order to detect a heat transfer characteristic of the sample that is indicative of a composition of the sample.

In an embodiment, there is provided a method of detecting contamination of a liquid, comprising: providing a resistive element in direct contact with the liquid; heating the resistive element by driving an electrical current through the resistive element; measuring a change in resistance of the resistive element caused by the heating; analysing a relationship between the amount of heat supplied to the resistive element during the heating and the measured change in resistance of the resistive element in order to detect a change in a heat transfer characteristic of the liquid that is indicative of contamination of the liquid.

According to an embodiment, the method comprises measuring the resistance of the resistive element while the resistive element is heated through a range of temperatures that contains the boiling point of a predetermined contaminant; and detecting features in the measured resistance that are characteristic of the formation of a vapour of the predetermined contaminant, thereby detecting a presence of and/or an amount of the predetermined contaminant in the liquid. As described above, the heat transfer characteristics of the liquid before vaporisation of the predetermined contaminant may be significantly different from the heat transfer characteristics of the liquid after vaporisation of the predetermined contaminant. This difference will show up in the measured variation of the resistance as the resistive element is heating through the boiling point, thereby provided a sensitive measure of a presence of, and/or of an amount of, the predetermined contaminant.

In an embodiment the predetermined contaminant is water. Water is a common contaminant and can be detrimental in many situations. For example mixing of water with a lubricating oil can cause the formation of colloids which greatly reduce the lubricating performance of the oil.

Embodiments of the invention will now be described, by way of example only, with reference to the accompanying drawings in which corresponding reference symbols indicate corresponding parts, and in which:

FIG. 1 is a schematic side sectional view of an embodiment of an apparatus for detecting contamination of a liquid in which the lower part of the figure is a magnified view of the region circled by the broken line circle in the upper part of the figure;

FIG. 2 depicts a first probe element having a first-probe-element heater located at a first surface of the first probe element;

FIG. 3 depicts a first probe element having a first-probe-element heater located at a second surface of the first probe element;

FIG. 4 is a schematic side sectional view of a portion of an alternative embodiment of an apparatus for detecting contamination in a liquid corresponding to the lower part of FIG. 1 but in which two probe elements are provided;

FIG. 5 is a schematic side sectional view of a further alternative embodiment of an apparatus for detecting contamination of a liquid comprising a resistive element;

FIG. 6 depicts an alternative example configuration for the resistive element;

FIG. 15 is a schematic side sectional view of two thin film resistive elements encapsulated in a support material and sandwiched between a substrate and a solid sample;

FIG. 16 is a schematic top view of two resistive element assemblies;

FIG. 17 is a schematic side sectional view of two thin film resistive elements encapsulated in a support material and connected to a sample;

FIG. 18 is a schematic side sectional view of a flexible resistive element assembly attached to a curved surface of a sample.

Figure 7:
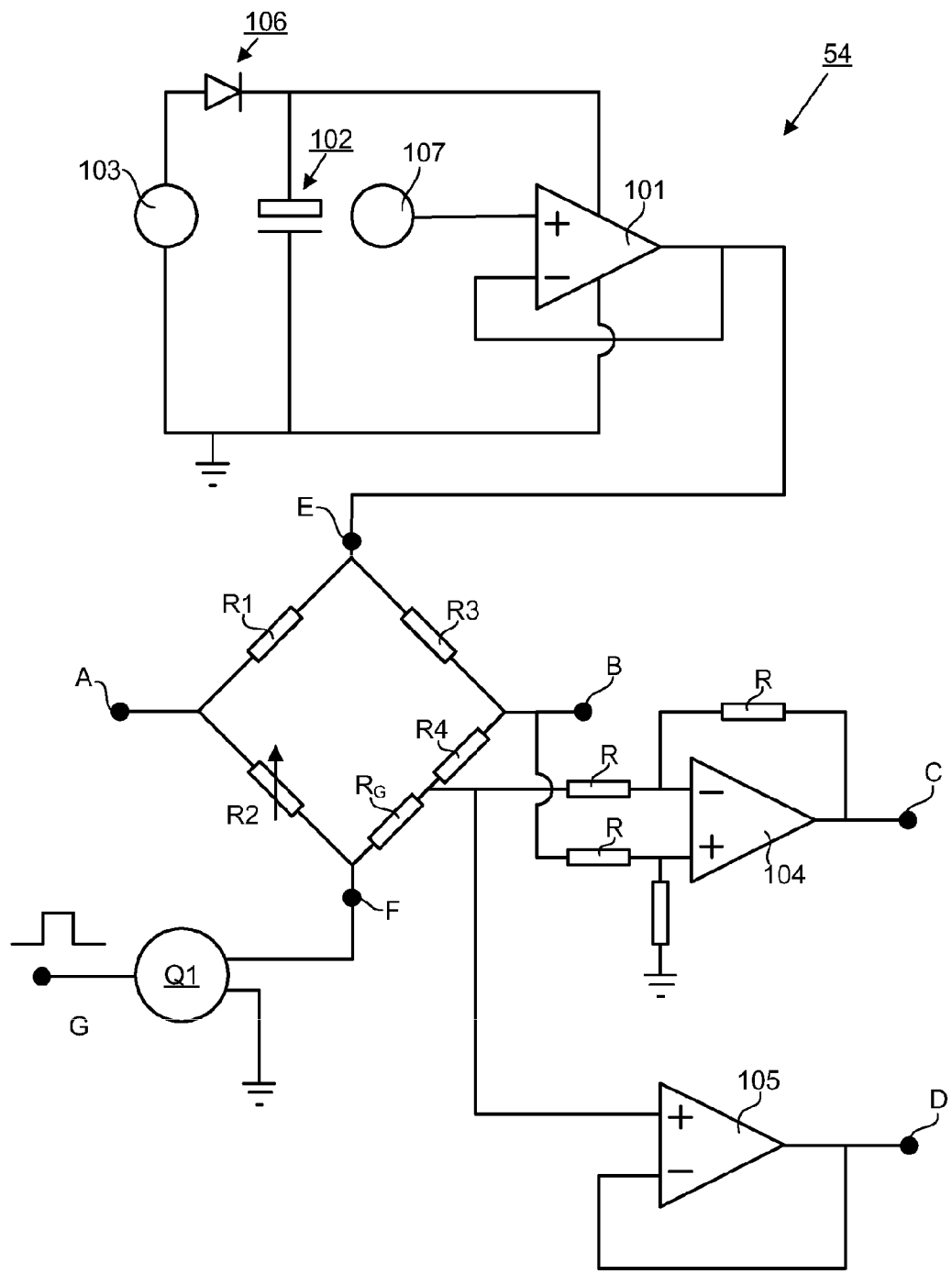
FIG. 7 depicts an example measurement system for detecting contamination in a liquid using a resistive element.

The present inventors have recognised that the heat transfer characteristics of materials (e.g. thermal conductivity, k specific heat capacity, c, and quantities that depend on one or both of these properties) can depend sensitively on the composition (e.g. chemical or structural) of the materials. In the case of liquids for example, the heat transfer characteristics may depend sensitively on a level of contaminants in the liquids. The thermal product, $\sqrt{pck}$, where p is equal to the density, is often a heat transfer characteristic that is particularly sensitive to composition (e.g. contamination) because it takes into account both k and c. Changes in either or both of k and c will typically result in a change in $\sqrt{pck}$. The table below shows representative values for these quantities for water, mineral oil and insulation oil. The large difference in $\sqrt{pck}$ for water compared with $\sqrt{pck}$ for either of the oils suggests that detection of water contamination in oil can be performed sensitively by measuring changes in heat transfer characteristics. However, there is also a significant difference in $\sqrt{pck}$ between the two types of oils. As will be seen, such differences make it possible for changes in the state or composition of oils (and other liquids) other than contamination by water to be detected by measuring changes of heat transfer characteristics of the liquids.

| | Temp °C. | Density $Kgm^{-3}$ $\rho$ | Specific heat capacity $JKg^{-1}K^{-1}$ c | Thermal conductivity $Wm^{-1}K^{-1}$ κ | Thermal product $(J^2m^{-4}K^{-2}s^{-1})^{1/2}$ $\sqrt{\rho c \kappa}$ |
|---|---|---|---|---|---|
| Water | 60 | 983 | 4184 | 0.580 | 1558 |
| Mineral oil | 60 | 868 | 2010 | 0.140 | 494 |
| Insulation oil | 60 | 842 | 2090 | 0.120 | 460 |

Contamination by water has been mentioned above. Oils may also be contaminated by metals and carbon (which can be added to the oil due to wear of moving parts). Metallic materials and carbon have a significantly higher thermal conductivity and specific heat capacity than oil. For example, steel typically has a thermal conductivity of about 46 W/mK, carbon steel about 54 W/mK, carbon about 2 W/mK and nickel about 91 W/mK.

The effect of contamination on the heat transfer characteristics of a liquid may not be derivable simply by summing the individual heat transfer characteristics of the components of the liquid. This is because the contamination may lead to the formation of multi-phase compositions having complex thermal properties. However, for many contaminants there will, overall, be a distinct change in the heat transfer characteristics that is attributable to the contamination and which will form an effective basis for detecting the contamination.

The present inventors have recognised that detecting changes in heat transfer characteristics of materials (e.g. liquids) over time can provide a simple, effective and reliable way to detect changes in the composition of the materials (e.g. contamination of liquids).

In an embodiment, there is provided an apparatus 2 for detecting a composition of a sample, such as contamination of a liquid 10. An example of such an apparatus 2, where adapted to detect contamination of a liquid, is depicted in FIG. 1. In this embodiment the apparatus 2 comprises a first probe element 14. The first probe element 14 may comprise a block of material of known heat transfer characteristics for example. The first probe element 14 may be elongate (but this is not essential). In this example the first probe element 14 penetrates through a containing wall 8 containing the liquid 10. An insulating material 16 is provided to insulate the first probe element 14 thermally from the containing wall 8. In other embodiments, instead of penetrating through the containing wall 8, the first probe element 14 may simply be connected to the wall 8 or embedded into the wall 8 (again with suitable insulation provided to insulate the first probe element 14 thermally from the containing wall 8). The containing wall 8 (for any embodiment) may for example be the wall of a sump for containing a lubricating oil for a machine with moving parts, such as an engine or gearbox. Alternatively or additionally, the containing wall 8 (for any embodiment) may form part of a conduit for a flow of the liquid. Alternatively or additionally, the containing wall (for any embodiment) may form part of a container for fuel such as petrol, diesel or kerosene. The first probe element 14 is configured to provide a first surface 31 in direct contact with the sample, in this case liquid 10. For example, the first surface 31 may be formed at an end of the first probe element that is facing the sample or liquid 10; the "direct contact" may occur via a thin element such as a temperature sensor or a protective film or a thin film of support material such as a thin electrically insulating material, if this is provided. The first probe element 14 further comprises a second surface 32 that is not in direct contact with the sample, in this case liquid 10. For example, the second surface 32 may be formed at the other end of the first probe element, facing away from the sample or liquid 10 and/or separated from the sample or liquid 10 by a main body of the first probe element). Heat passing from the first surface 31 to the second surface 32 must pass through substantially the whole length of the first probe element 14.

A measurement system is provided that is configured to measure a rate of heat transfer through the first surface 31. A processing unit 4 is provided that is configured to analyse the measured rate of heat transfer in order to detect a heat transfer characteristic that is indicative of a composition of the sample. In this particular example, the processing unit 4 may be configured to detect a change in a heat transfer characteristic of the liquid 10 that is indicative of contamination of the liquid 10. The efficiency with which heat is transferred from the sample (e.g. liquid 10) to the first surface 14 depends on the heat transfer characteristics of the sample (e.g. liquid 10). Therefore changes in the heat transfer characteristics caused by contamination will lead to changes in the measured rate of heat transfer through the first surface relative to what would be expected were the liquid uncontaminated, all other factors being equal.

FIG. 1 is an example of a type of embodiment in which the measurement system comprises a first surface temperature sensor 21 configured to measure a temperature at the first surface (which shall be referred to hereinafter as a "first temperature"). The measurement system in this type of embodiment further comprises a second surface temperature sensor 22 configured to measure a temperature at the second surface 32 (which shall be referred to hereinafter as "second temperature"). The measurement system in this type of embodiment is configured to use the measured first and second temperatures to measure the rate of heat transfer through the first surface 31.

In the example of FIG. 1 the rate of heat transfer may be determined as follows.

The first probe element 14 is of known dimensions and known thermal conductivity. Therefore the rate of heat transfer through the first probe element 14 can be calculated from the standard expression:

$$\dot{q} = -\kappa \frac{dT}{dx} \quad [1]$$

where $\dot{q}$ is the rate of heat transfer in W/m², k is the thermal conductivity in W/mK and dT/dx is the temperature gradient in K/m. Measurements using the first and second surface temperature sensors 21 and 22 provide dT/dx and K is known, so $\dot{q}$ can readily be obtained. $\dot{q}$ can then be equated to the heat transfer from the sample (e.g. liquid 10) to the first probe element 14 using the expression:

$$\dot{q} = -h(T_L - T_1)$$

where h is the surface heat transfer coefficient in W/m²K, $T_L$ is the temperature of the sample (e.g. liquid) and $T_1$ is the first temperature (measured by the first surface temperature sensor 21).

In an embodiment, the measurement system comprises, or is configured to receive input from, a sample temperature sensor 25 configured to measure the temperature of the sample (e.g. liquid) $T_L$. Equation [2] can then be used to obtain a value for h. This calculation may be performed by the processing unit 4 for example. In an embodiment, the obtained value for h is compared by the processing unit 4 to an expected value for h for uncontaminated sample (e.g. liquid) and/or to expected values for h for sample (e.g. liquid) that has been contaminated by a known amount and/or with known types of contaminant. The expected values may be obtained by reference to the results of calibration measurements, for example using a look-up table. Alternatively or additionally, the obtained value for h may be compared to one or more values (or average values) for h obtained at previous times in order to detect changes in h. The comparison is used to determine how the sample (e.g. liquid) is contaminated (e.g. quantity and/or type of contaminants) and/or to detect a change in the level of contamination. If the contamination is determined to be of an unacceptable nature (e.g. too much contamination and/or contamination of a type that indicates that particular problems may be occurring), the processing unit 4 may take certain predetermined actions. The processing unit 4 may output a signal indicating detection of contamination of the sample (e.g. liquid), which can be used by other devices in a variety of ways. The predetermined actions may include issuing an alarm signal or causing shutdown of the apparatus that depends on or uses the sample (e.g. liquid). In the context of lubricated oil for an engine or gearbox for example, the predetermined action may comprise indicating to a user that a service should be carried out to replace the lubricating oil.

In an embodiment, the apparatus 2 further comprises a first-probe-element heater 26 configured to heat the first probe element 14. Example configurations are shown in FIGS. 2 and 3. In an embodiment, the first-probe-element heater 26 is located at the first surface 31 (as in FIG. 2) or at the second surface 32 (as in FIG. 3). In an embodiment the first-probe-element heater 26 is used to modify the temperature difference between the first surface 31 and the sample (e.g. liquid 10) and thereby change the rate of transfer of heat from the sample (e.g. liquid 10) to the first surface 31. This may be useful for example where the temperature difference in the absence of the heating would be relatively small. Increasing the temperature difference in these circumstances may increase the accuracy of the determination of the rate of heat transfer and therefore improve the sensitivity of the detection of contaminants. As will be described below, when used in a system having a plurality of the probe elements, the first-probe-element heater 26 may also be used to remove or reduce the requirement to measure the temperature of the sample (e.g. liquid) in order to obtain h (assuming that the sample in contact with each of the probe elements is at least approximately the same).

In an embodiment, one or more contaminants of interest may have a boiling point which is within a range of temperatures achievable by heating a probe element. An example of such a contaminant of interest is water. For example, contamination of lubricating oil by water is a commonly encountered problem. Contamination by water can significantly disrupt the performance of the oil, for example by forming a colloid. In such embodiments, the following method can be performed, optionally using a first-probe-element heater 26 as described above to provide the heating. In a first step a rate of heat transfer through the first surface 31 is measured at a temperature at the first surface 31 that is below the boiling point of a predetermined contaminant (e.g. water). In a second step a rate of heat transfer through the first surface 31 is measured at a temperature at the first surface 31 that is above the boiling point of the predetermined contaminant (e.g. water). The detection of the change in the heat transfer characteristic of the sample (e.g. liquid) may in this embodiment comprise comparing the measured rate of heat transfer at the temperature at the first surface 31 that is below the boiling point of the predetermined contaminant (e.g. water) with the measured rate of heat transfer at the temperature at the first surface 31 that is above the boiling point of the predetermined contaminant (e.g. water). It is expected that the heat transfer characteristics of the sample (e.g. liquid) will depend sensitively on whether the predetermined contaminant is present. By heating the first surface 31 above the boiling point of the predetermined contaminant the amount of the predetermined contaminant present, if any, near the first surface 31 will be greatly reduced. If there is a significant amount of the predetermined contaminant in the sample (e.g. liquid) we should expect a large difference in heat transfer characteristics between the measurements carried out below and above the boiling point of the predetermined contaminant. For example, in the case where the predetermined contaminant is water, it is noted that the conductivity of water vapour is significantly lower than that of water (of the order of 36 times lower). Therefore, even relatively low levels of water should produce a relatively large output for detection. Furthermore, the transition from water to vapour should be relatively violent, providing a relatively easy to detect feature (e.g. a step or time-varying instabilities) in the output signal. Example data showing the effects of water contamination are discussed below with reference to the experimental results illustrated in FIGS. 11 and 12. This approach provides a highly sensitive way of detecting contamination by predetermined contaminants that can be vaporised, such as water. The approach also makes it easier to distinguish between changes of heat transfer characteristics of the sample (e.g. liquid) caused by metallic impurities only and changes of heat transfer characteristics of the sample (e.g. liquid) caused by other contaminants (e.g. water).

In an alternative embodiment, multiple probe elements having the same size and shape of surface in contact with the sample (e.g. liquid) are provided. The multiple probe elements may also have the same overall size and shape. The multiple probe elements are provided in relatively close proximity to each other such that in use the sample (e.g. liquid) in contact with each probe element is at the same temperature. In such an arrangement, by arranging for $\dot{q}$ to be different for two or more of the probe elements it is possible to obtain h without measuring $T_L$. This improves the simplicity of operation and/or construction, improves reliability and/or longevity, and/or reduces manufacturing costs. FIG. 4 is an example of an embodiment of this type in which two probe elements are provided and in which 4 is arranged to be different for each of the two probe elements by heating one of the probe elements.

FIG. 4 shows the provision of a second probe element 28 in addition to the first probe element 14. The first and second probe elements 14 and 28 are thermally insulated from each other and from the containing wall 8 by insulating material 16. The second probe element 28 has a third surface 33. The second probe element 28, like the first probe element 14, may or may not penetrate through the containing wall 8. The third surface 33 is arranged to be in direct contact with the sample (e.g. liquid 10). The second probe element 28 has a fourth surface 34 that is not in direct contact with the sample (e.g. liquid 10). The third and fourth surfaces correspond respectively to the first and second surfaces 31 and 32 of the first probe element 14 and may be configured in the same manner.

In the embodiment shown the measurement system comprises a third surface temperature sensor 23 configured to measure a third temperature of the third surface 33 and a fourth surface temperature sensor 24 configured to measure a fourth temperature of the fourth surface 34. The measurement system can use outputs from the third and fourth surface temperature sensors 23 and 24 to measure the rate of heat transfer through the third surface 33 (using expression [1] above). The processing unit 4 is configured to analyse the measured rates of heat transfer through the first and third surfaces 31 and 33 to detect the heat transfer characteristic of the sample (e.g. liquid 10) that is indicative of the composition of the sample (e.g. liquid 10) or the change in the heat transfer characteristic of the sample (e.g. liquid 10) that is indicative of contamination of the sample (e.g. liquid 10).

In the embodiment shown, the first probe element 14 comprises a first-probe-element heater 26. In other embodiments, the second probe element 28 also comprises a heater (which may be referred to as a "second-probe-element heater"). The second-probe-element heater may be configured in any of the ways that the first-probe-element heater 26 may be configured, as discussed above with reference to FIGS. 2 and 3.

In embodiments having first and second probe elements 14 and 28, such as that of FIG. 4, the respective rates of heat transfer, $\dot{q}_{p1}$ and $\dot{q}_{p2}$, between the sample (e.g. liquid 10) and each of the two probe elements 14 and 28 may be given by equations [3] and [4] below.

$$\dot{q}_{p1} = -h_1(T_L - T_1) \quad [3]$$

$$\dot{q}_{p2} = -h_2(T_L - T_3) \quad [4]$$

In the example of FIG. 4, where the first probe element 14 is heated, the third surface temperature $T_3$ will be lower than the first surface temperature $T_1$. $\dot{q}_{p1}$ and $\dot{q}_{p2}$ will therefore be different from each other. If both probes elements 14 and 28 are the same design and any flow (e.g. of liquid) past them is the same then the heat transfer coefficients will be the same (i.e. $h_1 = h_2 = h$). This provides two equations in two unknowns, h and $T_L$. Thus, h can be determined (without any separate measurement of $T_L$).

In an alternative approach $T_L$ is measured but only one of the second and fourth surface temperatures are measured (such that only one of $\dot{q}_{p1}$ and $\dot{q}_{p2}$ is available). The two unknowns in this case would be h and one of $\dot{q}_{p1}$ and $\dot{q}_{p2}$, again allowing h to be obtained. In this case, apparatus for measuring the second and fourth surface temperatures can be simplified (by only requiring that one of the two temperatures is measured). In such an embodiment $T_L$ can either be measured or derived from calibration and the definition of a lookup table.

In the embodiment of FIG. 4, different $\dot{q}_{p1}$ and $\dot{q}_{p2}$ are obtained by heating one of the probe elements and not the other of the probe elements. This is not essential. Different $\dot{q}_{p1}$ and $\dot{q}_{p2}$ could also be obtained by heating both of the probe elements but by different amounts, cooling one of the probe elements and heating the other of the probe elements, cooling one of the probe elements but not the other of the probe elements, or cooling both of the probe elements but by different amounts. Alternatively or additionally, the two probe elements could be formed from different materials (having different thermal conductivities). For example the first probe element 14 could be formed from a metallic material and the second probe element 28 could be formed from a ceramic material. Forming the probe elements 14,28 from different materials makes it possible to achieve different $\dot{q}_{p1}$ and $\dot{q}_{p2}$ even where neither of the probe elements 14,28 is heated (although heating could also be applied to increase the size of the difference between $\dot{q}_{p1}$ and $\dot{q}_{p2}$, which may improve accuracy).

The use of multiple probes may additionally or alternatively be used to improve accuracy by providing independent measurements of h. This approach may be particularly effective where the multiple measurements are incorporated into a bridge arrangement so as to provide a differential output.

In an embodiment the apparatus 2 further comprises a magnet 72 configured to attract magnetic or magnetisable particles preferentially to a region adjacent to a selected one of the first surface 31 and the second surface 33. For example, the magnet 72 may be positioned closer to the first surface 31 than the second surface 33 and/or orientated so as to apply a stronger magnetic field in the region of the first surface 31 than in the region of the second surface 33 (e.g. such that a magnitude of the magnetic field from the magnet 72 averaged over the first surface 31 is higher than a magnitude of the magnetic field from the magnet 72 averaged over the second surface 33). An example of such an arrangement is shown in FIG. 4. The magnet 72 improves the sensitivity with which magnetic or magnetisable particles may be detected. The magnet 72 may be particularly effective for detecting the presence of magnetic or magnetisable particles in a sample in which such particles are mobile (e.g. a liquid). The magnet 72 may be particularly effective for detecting contamination of a liquid with magnetic or magnetisable particles. In an embodiment, a comparison is made between a measurement of a rate of heat transfer through the surface (e.g. first surface 31) adjacent to which the magnetic or magnetisable particles are preferentially attracted and a rate of heat transfer through the surface (e.g. third surface 33) to which the magnetic or magnetisable particles are not preferentially attracted. Where significant quantities of the magnetic or magnetisable particles are present a large difference between the heat transfer through the respective surfaces is expected.

In an embodiment the first probe element 14 is compliant to allow the first surface 31 to deform and conform with a surface (e.g. a non-planar surface) of the sample when the sample is pressed against the first probe element 14. Embodiments of this type facilitate application to solid samples which do not have surfaces which naturally conform to the first surface 31. Making the first probe element 14 compliant helps reproducibly to achieve good thermal contact between the first surface 31 and the sample, for example by avoiding other materials or air gaps being present between the first surface 31 and the sample.

In the embodiment described above with reference to FIG. 4, the first-probe-element heater 26 and the first surface temperature sensor 21 are shown as separate elements. This is not essential. In other embodiments a single resistive element is configured to act as first-probe-element heater 26 and first surface temperature sensor 21. In an embodiment, the resistive element comprises a thin film resistive element, optionally encapsulated in a support material such as an electrically insulating film.

In an embodiment, an example of which is depicted in FIG. 5 for a case where the sample is a liquid 10, there is provided an apparatus for detecting a composition of a sample. In the particular example of FIG. 5 the apparatus is configured to detect contamination of the liquid 10. The apparatus comprises one or more resistive elements 50. Each resistive element 50 is configured to be in thermal contact with a sample (e.g. liquid 10). The resistive element 50 may for example be in direct contact or contact via a support material, for example a thin element such as a protective film or electrically insulating film. As in the embodiments discussed above the sample (e.g. liquid 10) may be contained by a containing wall 8 for example, such as a sump for lubricating oil, a fuel container, or a conduit for a flow of the liquid. In an embodiment a measurement system 54 is provided configured to 1) drive an electrical current through each of the one or more resistive elements 50 in order to supply heating at each of the one or more resistive elements 50, and 2) measure a change in a resistance of each of the one or more resistive elements 50. One or more of the resistive elements 50 may be a resistance thermometer for example, having a predetermined calibration accurately linking a temperature of the resistive element 50 to a resistance of the resistive element. A processing unit 4 analyses a relationship between the amount of heat supplied to the each of the one or more resistive elements 50 and the change in the resistance (and therefore temperature) of each of the one or more resistive elements 50 in order to detect a heat transfer characteristic of the sample that is indicative of a composition of the sample. In the example of FIG. 5 where contamination is being detected the processing unit 4 detects a change in a heat transfer characteristic of the liquid 10 that is indicative of contamination of the liquid.

In an embodiment a pulse of heating may be applied. A response to the pulse of heating may be compared with the response to the same pulse applied to a reference sample (e.g. liquid) (which may for example be the sample being monitored at a previous time). The size of the response, the variation of the response as a function of time, or various other aspects of the response may be considered. Any deviation from the response to the same pulse applied to the reference sample may indicate contamination of the sample or another deviation of the chemical or structural composition of the sample from what is expected or desired. The size or time dependence of the deviation may be indicative of the type of deviation or contamination or the magnitude of deviation (e.g. amount of contamination). The nature of the heating may be varied to tune the sensitivity of the detection process. In the case where contamination is being detected the sensitivity of the detection process may be tuned so as to be generally higher for all contaminants or so as to be more sensitive for certain selected contaminants at the expense of being less sensitive to other contaminants. The nature of the heating may be varied for example by changing the shape, size, duration or repetition rate of a heating pulse or series of pulses, for example.

In an embodiment the resistive element is mounted on a substrate in such a way that at least 10% of the surface area of the resistive element is in contact with the substrate, optionally via a support material encapsulating the resistive element (e.g. a thin film of electrically insulating material), optionally more than 30%, optionally around 50%. In an embodiment the resistive element 50 is a thin film resistive element (e.g. thin film resistance thermometer). In an embodiment the resistive element comprises a thin film of platinum mounted on a substrate. In an embodiment the substrate comprises low-thermal-expansion borosilicate glass.

In an embodiment, one or more of the resistive elements 50 is a thin film resistive element having a first surface 51 facing towards the sample (e.g. liquid 10) and a second surface 53 facing towards the substrate 52. It is understood that the first and second surfaces 51 are the large surfaces of the thin film (and do not include any of the very thin side surfaces). In an embodiment no portion of the sample is present between the second surface 53 and the substrate 52. The second surface 53 is either in contact with the substrate 52 without any intervening layer or in contact via a support material such as a thin electrically insulating film.

In embodiments of this type a surface of the substrate directly adjacent to a thin film resistive element 50 is an example of a first surface of a first probe element. The first surface is in direct contact with the sample via the thin film resistive element (and any support material such as a thin electrically insulating film which may encapsulate the thin film resistive element 50). The driving of the electrical current through the thin film resistive element 50 and the measurement of the change in resistance of the thin film resistive element provide a measure of a rate of heat transfer through the first surface because the change in resistance that is observed will depend directly on the rate of heat transfer through the first surface.

In an embodiment one or more of the resistive elements is encapsulated in a support material such as an electrically insulating film.

Figure 13:
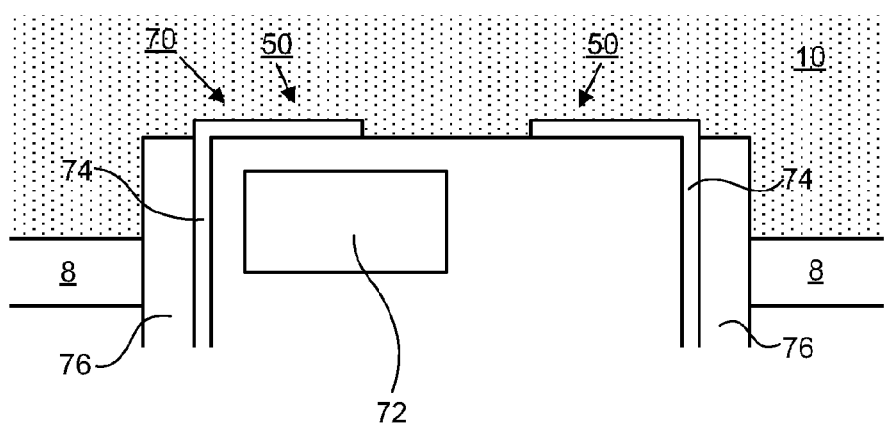
FIG. 13 is a schematic side sectional view of a plug comprising two thin film resistive elements and a magnet.
Figure 14:
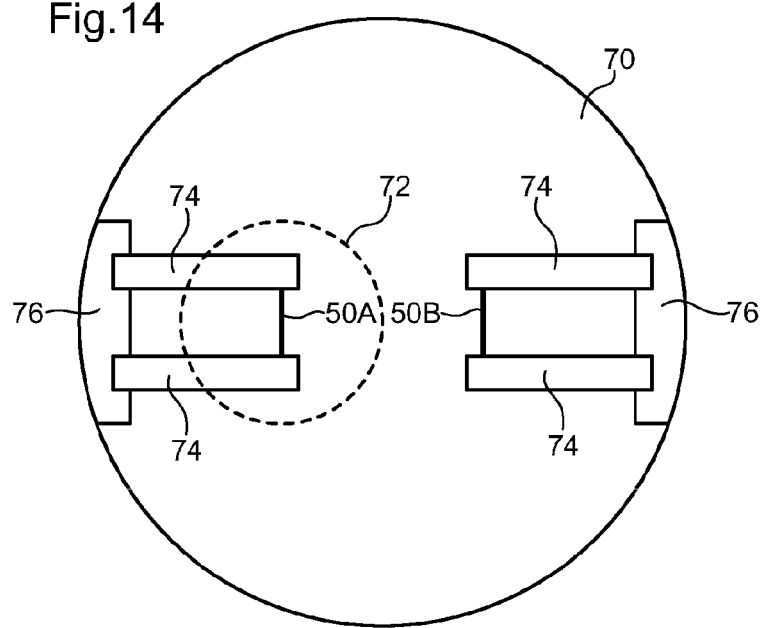
FIG. 14 is a schematic top view of the plug of FIG. 13.

FIGS. 13 and 14 depict a further example of an apparatus for detecting a composition of a sample (e.g. liquid 10) comprising one or more resistive elements 50. In this particular example two resistive elements 50 are provided: a first resistive element 50A and a second resistive element 50B. In this example each of the resistive elements 50A,50B is a thin film resistive element. The resistive elements 50A,50B are mounted on a plug 70 configured for mounting on or in a containing wall 8 containing the sample (in this case liquid 10). The plug 70 acts as the substrate in this embodiment. A recess 76 is provided in the plug to allow electrical tracks 74 to be brought from a region outside of the containing wall 8 to the resistive elements 50A,50B for driving the electrical current through the resistive elements 50A,50B and measuring the changes in resistance of the resistive elements 50A,50B. The recess 76 may be filled with an insulating material for example to allow the plug to seal. A magnet 72 is provided for attracting magnetic or magnetisable particles preferentially to a region adjacent to a selected one of the first resistive element 50A and the second resistive element 50B (in this particular example to the first resistive element 50A). For example, the magnet 72 may be positioned closer to the first resistive element 50A than the second resistive element 50B and/or orientated so as to apply a stronger magnetic field in the region of the first resistive element 50A than in the region of the second resistive element 50B (e.g. such that a magnitude of the magnetic field from the magnet 72 averaged over the first resistive element 50A is higher than a magnitude of the magnetic field from the magnet 72 averaged over the second resistive element 50B). The magnet 72 improves the sensitivity with which magnetic or magnetisable particles may be detected. The magnet 72 may be particularly effective for detecting the presence of magnetic or magnetisable particles in a sample in which such particles are mobile (e.g. a liquid). The magnet 72 may be particularly effective for detecting contamination of a liquid with magnetic or magnetisable particles. In an embodiment, a comparison is made between a measurement of a rate of heat transfer through a surface on which the first resistive element 50A is mounted and a rate of heat transfer through a surface on which the second resistive element 50B is mounted. Where significant quantities of the magnetic or magnetisable particles are present a large difference is expected. In an embodiment a comparison is made between the relationship between the amount of heat supplied to the first resistive element 50A and the change in the resistance of the first resistive element 50A and the amount of heat supplied to the second resistive element 50B and the change in the resistance of the second resistive element 50B. Where significant quantities of the magnetic or magnetisable particles are present a large difference is expected.

FIGS. 15 and 16 depicts a further example comprising resistive elements 50. In this example a first resistive element assembly 86 is provided in which a first resistive element 50A is a thin film resistive element and conductive tracks 90 and 92 provide electrical connections to the first resistive element 50A. The first resistive element 50A and conductive tracks are encapsulated within a support material 84 provided in the form of a flexible, thin, insulating film. In an embodiment the first resistive element assembly 86 as a whole is also flexible. A second resistive element assembly 88 is provided in which a second resistive element 50B is a thin film resistive element and conductive tracks 90 and 92 provide electrical connections to the second resistive element 50B. The second resistive element 50B and conductive tracks are encapsulated within a support material 84 provided in the form of a flexible, thin, insulating film. In an embodiment the second resistive element assembly 86 as a whole is also flexible.

The first and second resistive element assemblies 86,88 are mounted on a substrate 52, thus mounting the first and second resistive elements 50A,50B onto the substrate 52 via the support material 84. In an embodiment, the first and second resistive element assemblies 86,88 may be adhered to the substrate 52. A sample 82 is provided on a surface of the first and second resistive element assemblies 86,88 opposite to the substrate 52. The first and second resistive element assemblies 86,88 are thereby sandwiched between the sample 82 and the substrate 52. A surface of the substrate 52 directly adjacent to the first resistive element 50A is an example of a first surface 31 of a first probe element. The first surface 31 is in direct contact with the sample 82 via the first resistive element 50A and the support material 84. Driving of an electrical current through the first resistive element 50A and measurement of the change in resistance of the first resistive element 50A provide a measure of a rate of heat transfer through the first surface 31 because the change in resistance that is observed will depend directly on the rate of heat transfer through the first surface 31. Similarly, a surface of the substrate 52 directly adjacent to the second resistive element 50A is an example of a third surface 33 of a second probe element. The third surface 33 is in direct contact with the sample 82 via the second resistive element 50B and the support material 84. Driving of an electrical current through the second resistive element 50B and measurement of the change in resistance of the second resistive element 50B provide a measure of a rate of heat transfer through the second surface 33 because the change in resistance that is observed will depend directly on the rate of heat transfer through the second surface 33.

In an embodiment the one or more resistive elements 50 and the substrate 52 are compliant to allow the first surface 31 to deform and conform with a surface of the sample 82 when the sample 82 is pressed against the resistive element 50 (optionally via a support material 84), while maintaining a thermal contact between the resistive elements and the substrate.

FIG. 17 depicts an alternative embodiment where the first and second resistive element assemblies 86,88 are connected to the sample 82 (e.g. by adherence) or pressed against the sample 82 but where no substrate 52 is provided. The sides of the first and second resistive element assemblies 86,88 may instead be left open to air. In this case, the air acts as the substrate 52. Heat generated in the resistive elements 50A,50B will dissipate into the air instead of into a substrate 52. Sensitive measurements of the thermal properties of the sample will still be possible as long as the thermal properties of the air are not too dissimilar from the thermal properties of the sample 82. This arrangement may be particularly convenient where the sample 82 has a curved surface because only the first and second resistive element assemblies 86,88 need to be made to conform with the curved surface. It is not necessary for example to arrange also for a substrate 52 to conform with the curved surface. This arrangement is also structurally simple and compact.

The embodiment of FIGS. 15-17 comprises two resistive elements 50A, 50B but this is not essential. In other embodiments a single resistive element or more than two resistive elements are provided.

FIG. 18 depicts an example of application of an embodiment of the type discussed above with reference to FIG. 17 to a sample 82 having a curved surface. In this particular example a single resistive element assembly 86 is shown but further resistive element assemblies could be provided.

Figure 10:
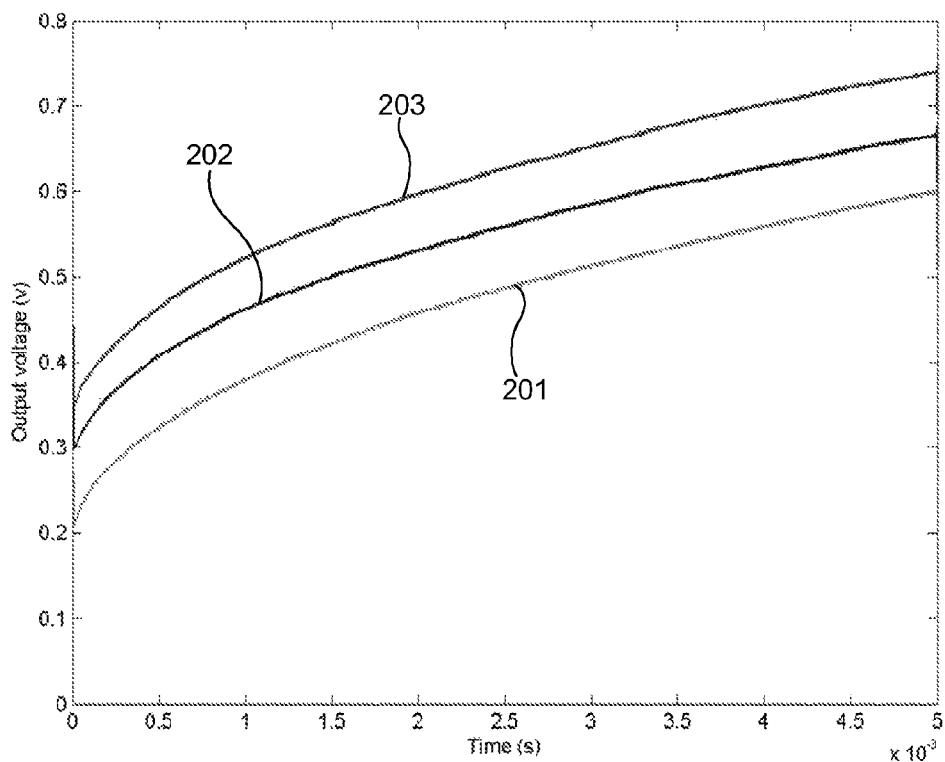
FIG. 10 is a graph showing responses of a platinum thin film resistive element to a heating pulse when in contact with three different liquids.

FIG. 10 depicts example data obtained using an embodiment in which the resistive element 50 comprises a thin film formed from platinum mounted on a machinable glass-ceramic substrate. The vertical axis shows an output voltage from the resistive element 50 during application of a heating pulse of constant electrical current (corresponding to 5V through a resistance of about 50 Ohms) to the resistive element. The vertical axis is proportional to the resistance of the resistive element 50, which in turn varies in a predetermined way as a function of the temperature of the resistive element 50. The horizontal axis measures time from 0 to 5 ms, which in this case corresponds to the duration of the heating pulse. The resistive element 50 was mounted flush against the substrate, so in this particular example approximately 50% of the surface area of the platinum film was exposed to the liquid being tested. The three curves shown in FIG. 10 illustrate respectively how the resistance (and thus temperature) of the resistive element 50 changed as a function of time during application of the heating pulse when the resistive element 50 was in contact with each of three different formulations of liquid. Curve 201 corresponds to the case where the liquid comprised oil only. Curve 202 corresponds to the case where the liquid comprised a mixture of oil and water. Curve 203 corresponds to the case where the liquid comprised a mixture of oil and small copper particles. As can be seen, the heights of the three curves 201-203 are markedly different despite the fact that identical heating pulses were applied in each case. The differences between the three curves 201-203 arise because of the different heat transfer characteristics of the liquids in each case. It follows that detection of contamination of an oil by water or copper particles (and, by extension, other contaminants) can be achieved by applying an identical heating pulse to the resistive element 50 when the resistive element 50 is exposed to the liquid under test and comparing the result with the curves of FIG. 10. For example, as contamination in this example tends to cause the temperature of the resistive element 50 to be higher during the heating pulse, detection of a temperature of the resistive element 50 that is above a predetermined threshold amount higher than the pure oil reference curve, at a predetermined time point during the heating pulse (or an average value), may be interpreted as indicating contamination that is above an acceptable amount.

In an alternative embodiment, the resistive element 50 comprises an element 60 that is mounted so as to be in direct contact with the sample (e.g. liquid 10) over most of the surface area of the element 60, optionally over more than 90% of the surface area, optionally over more than 95% of the surface area, optionally over more than 99% of the surface area. An example of such an element 60 is depicted in FIG. 6. The element 60 may comprise a wire (e.g. of about 100 micron diameter) or other elongate element. The element 60 may have a length which is substantially larger than its width (e.g. diameter in the case of a circular wire). For example, the length may be greater than 100 times the width or diameter of the element 60. The element 60 may be suspended between supports 62, for example, which may act as, or carry, electrodes. The supports/electrodes 62 may be many times more massive than the element 60 (and therefore have a heat capacity that is many times higher). Where the supports 62 act as electrodes, electrically insulating material 64 may be provided to isolate the electrodes from the wall 8 containing the sample (e.g. liquid 10). In an arrangement of this type a large majority or substantially all of the heat flow to and from the element 60 must be through the sample (e.g. liquid 10). It is possible to achieve very sharp thermal transitions in the element 60 and/or quickly produce vapour phases.

In an embodiment, the apparatus is configured to heat the element 60 to very high temperatures (e.g. 700-800K) in order to clean the surface of the element 60. For example, deposits such as oil-varnishing may be removed by pyrolising the element 60 at very high temperatures. If such deposits are not removed they could negatively affect the heat transfer measurements.

In an embodiment, the element 60 is heated through a range of temperatures that contains a boiling point of a predetermined contaminant (e.g. water). As described above the heat transfer characteristics of the liquid 10 before vaporisation of the predetermined contaminant may be significantly different from the heat transfer characteristics of the liquid 10 after vaporisation of the predetermined contaminant. A curve of resistance of the element 60 against time as the temperature of the element 60 is driven through the range of temperatures containing the boiling point of the predetermined contaminant will therefore show features that are characteristic of the particular predetermined contaminant concerned. For example, where the predetermined contaminant is water the curve will show features (such as steps or instabilities) as the temperature of the element 60 rises to a point which causes boiling of water adjacent to the element 60, thereby allowing identification of the presence of water. The size of the features may also provide information about the amount of the contaminant that is present.

As mentioned above, the measurement system 54 may be configured to deliver power to the resistive element (e.g. the element 60) by driving an electrical current through the element 60 at the same time as measuring the resistance (and therefore temperature, where a calibration is available) of the element 60. If the element 60 is made from platinum, for example, a very linear relationship between temperature and resistance is known.

The power, P, delivered to the element 60 may be expressed in terms of the current, I, driven through it and the resistance, R, of the element 60, as:

$$P = I^2 R \qquad [A]$$

where R is a function $f$ of temperature T as follows:

$$R = f(T) \qquad [B]$$

If the element 60 is driven with a fixed voltage pulse, for example, the temperature T can be derived by measuring I to determine R. $f(T)$ can be obtained from prior calibration measurements.

If the element 60 were heated (by a current) in a vacuum then the rate of rise of temperature would be given by equation [C] below.

$$T = T_0 + ((C_p \cdot m \cdot J) \cdot t) \qquad [C]$$

where $C_p$ is the specific heat capacity of the material forming the element 60, m is the mass of the element 60, J is the total energy input into the element 60, t is the time, $T_0$ is the initial temperature of the element 60 and T is the final temperature of the element 60.

The energy input from resistive heating is given by the following expression $$\int_t^0 I^2 R \, dt \qquad [D]$$

If the vacuum is replaced by a sample (e.g. liquid), there will also be a transfer of energy to the sample (e.g. liquid), given by $$\int_t^0 \dot{q} \, dt \qquad [E]$$

where $\dot{q}$ is the rate of heat transfer to the sample (e.g. liquid).

If the heat transfer period is relatively brief then the Nusselt number, $Nu_L$, given below, will tend to zero $$Nu_L = \frac{hL}{\kappa} \qquad [F]$$

where k is the thermal conductivity of the liquid, L is the characteristic length, and h is the convective heat transfer coefficient. This is important if measuring the heat transfer in dynamic liquids, such as in a gear box or oil pipe. The result of $Nu_L$ tending to zero is that to a good approximation it can be assumed that substantially all of the heat transfer is due to the heat transfer coefficient of the liquid. Furthermore, characteristics of good and poor liquid may be tested empirically with seeded defects (such as 1% water added) or by testing known used/defective samples.

The change in resistance/temperature of the resistive element caused by the heating will depend on the ability of the sample (e.g. liquid) to carry the heat away and therefore on the heat transfer characteristics of the sample (e.g. liquid). If the heat transfer characteristics of the sample (e.g. liquid) are different relative to a reference, for example changed due to contamination, then this will be detectable as a deviation in the relationship between the amount of heat supplied and the resulting change in resistance/temperature of the resistive element from what would be expected for the reference (e.g. an uncontaminated liquid).

Embodiments of the type shown in FIGS. 5 and 6 make it possible to simplify the part of the apparatus that is connected to the containing wall 8 for the liquid 10 (in comparison with embodiments of the type shown in earlier figures for example). However, more sophisticated electronics and/or calibration measurements may be needed to obtain the required accuracy.

In another embodiment, a second derivative of the heat transfer, q̈, may be obtained. q̈ may be defined as follows:

$$\ddot{q} \int_t^0 \dot{q} \, dt$$

The second derivation q̈ may reveal other useful characteristics of the sample (e.g. liquid). The second derivative q̈ may be obtained by applying a high pulse power to the element 60.

Example circuitry for a measurement system 54 configured to perform such measurements is shown in FIG. 7.

The following elements are shown in FIG. 7:
- 101 Power amplifier (e.g. about 10 A RATED)
- 102 Charge store (e.g. about 40,000 µF)
- 103 Power supply (e.g. about 30V DC)
- 104 Differential amplifier for I
- 105 Buffer amplifier for V
- R1+R2 Bridge balance
- R3+$R_G$ Active bridge half
- Q1 Power switch (e.g. fast, low resistance MOSFET)
- C Output of current I
- D Output of voltage V
- E High side of bridge
- F Low side of bridge
- G Signal pulse control
- R4 Current sense shunt (resistance) (e.g. 20 mΩ)
- A+B Diagnostic differential signal outputs for development
- 106 Diode rectifier
- 107 Voltage reference A voltage generated by voltage supply 103 is fed through a rectifier diode 106 to charge a high capacity storage 102. The storage 102 provides a high current power source to the power amplifier 101. A voltage reference 107 sets a high side voltage presented at E.

A bridge is created between the points A, E, B and F. In an example, R3 and $R_G$ are about 1.0 Ohms, and R1 and R2 are about 470 Ohms. A power switch device Q1 is provided to rapidly bring point F to ground under a signal pulse at G. The circuit enables a steady bridge voltage to be maintained without demanding a high gain bandwidth from the power amplifier 101. The power amplifier 101 needs only to maintain a DC level. High energy pulses of precise timing are made possible using a fast MOSFET power switch for Q1 at the low side of the bridge.

When the bridge is energised the differential voltage points (A & B) will provide a voltage corresponding to the Ohmic resistance change of the gauge element $R_G$ (e.g. the element 60 of the FIG. 6). The other resistors in the bridge are chosen to have a very low parts-per-million (ppm) change in resistance with temperature. Therefore observed bridge voltages are only a function of the gauge $R_G$.

For precise measurements of heat transfer to the element 60, and from the element 60 to the sample (e.g. liquid), the equations [C], [D], and [E] require a measurement of the voltage V and current I across the element 60. The current is determined from the output of the circuit at C. The voltage is determined from the output of the circuit at D. Thus the energy input and the corresponding rise in temperature can be determined and the heat transfer function to the sample (e.g. liquid) can be computed.

The total energy and energy rate can be controlled by varying the reference voltage 107 and the pulse duration at G. In a typical embodiment, a pulse will last a few milliseconds and will not be repeated for several hundreds of milliseconds.

The circuit allows a modest power source to store energy to deliver very high energy density pulses. Electronic controls will activate the power level and pulses duration whilst reading the voltage signals at C and D. The electronic controls may be provided by the measurement system 54 or the processing unit 4 (or both).

In an embodiment, fast ADC to storage in computer memory will be employed leaving time to compute the heat transfer data from which quantitative measurements can be performed and compared to calibrated lookup tables to provide qualitative assessments of the contamination characteristics of the sample (e.g. liquid) being tested. This functionality may for example be performed in the processing unit 4.

Figure 11:
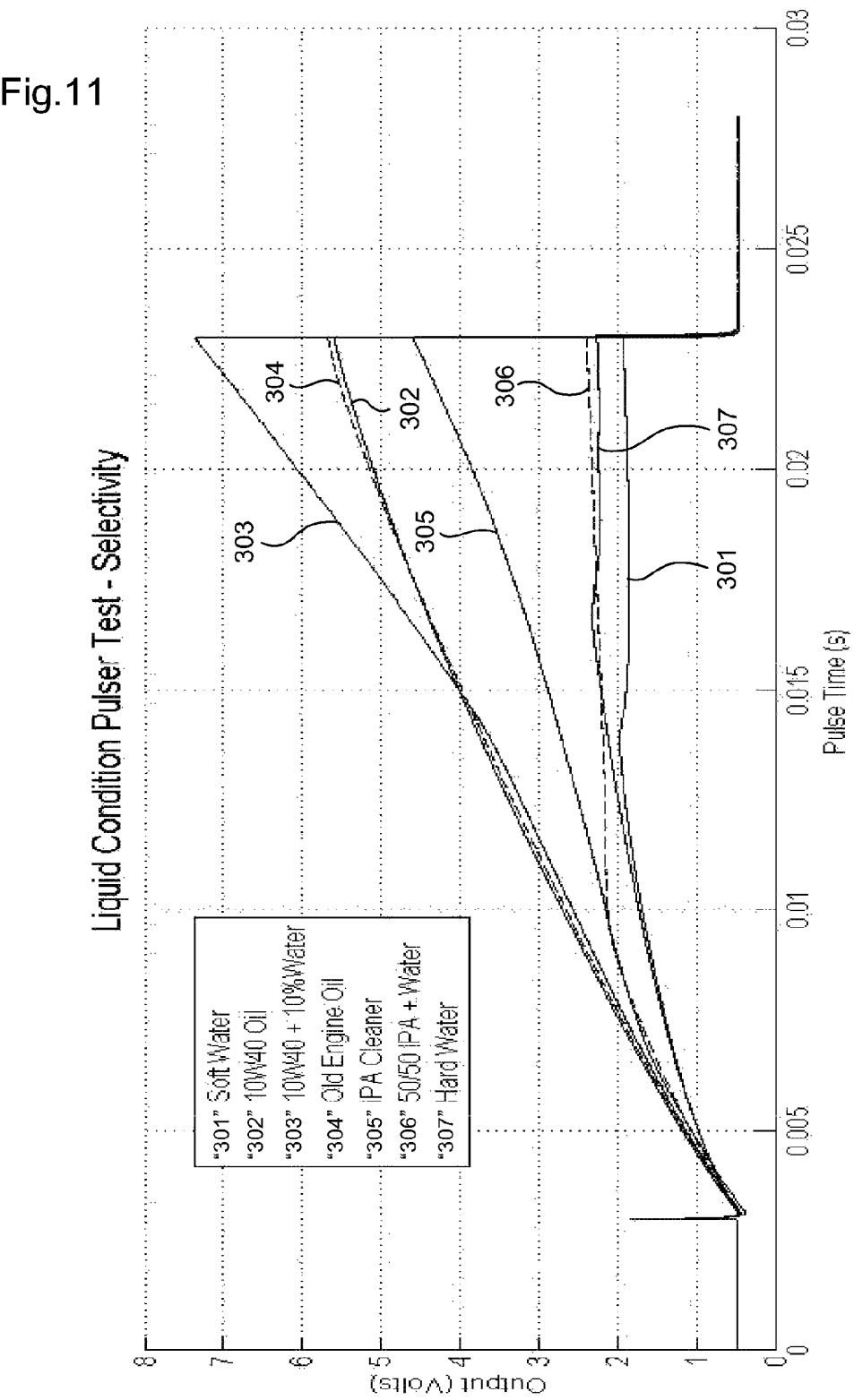
FIG. 11 is a graph showing changes of resistance with time during heating of a resistive element in different liquids.
Figure 12:
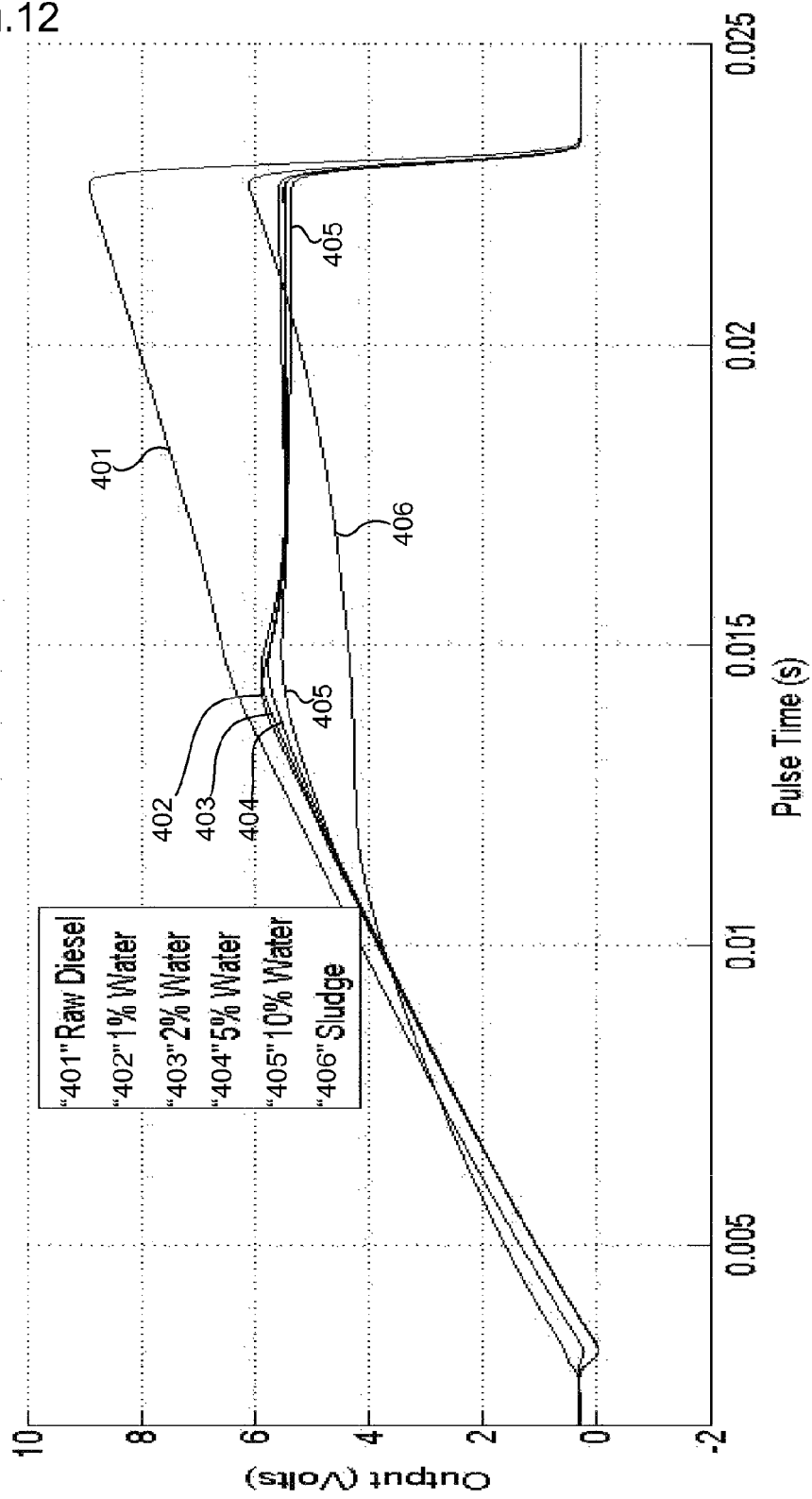
FIG. 12 is a graph showing changes of resistance with time during heating of a resistive element in diesel fuel comprising different amounts of contaminant.

FIGS. 11 and 12 show representative data showing the result of applying a heating pulse to a resistive element 50 of the type shown in FIG. 6 when exposed to a variety of different liquids. In this particular example, the resistive element 50 had the following characteristics: composition=99.9% Pt, diameter=100 microns, length=10 mm. Ambient resistance, R, of the resistive element 50 was R~0.14 Ohms. Heating the resistive element 50 by about 80 deg C. will raise the resistance to 0.1722 Ohms. On a bridge with 10× amplification this produces 2.05 Volts. Control electronics are provided to manage the power and avoid damage to the resistive element 50 which otherwise be caused by power instabilities or spikes. The vertical axes show an output voltage from the resistive element 50 during application of the heating pulse. The vertical axis is proportional to the resistance of the resistive element 50, which in turn varies in a predetermined way as a function of the temperature of the resistive element 50. The horizontal axis measures a time interval spanning application of the heating pulse.

The seven curves shown in FIG. 11 illustrate respectively how the resistance (and thus temperature) of the resistive element 50 changed as a function of time during application of the heating pulse when the resistive element 50 was in contact with each of seven different formulations of liquid. Curve 301 corresponds to the case where the liquid consisted of relatively soft water only. Curve 302 corresponds to the case where the liquid consisted of 10W40 oil only. Curve 303 corresponds to the case where the liquid consisted of a mixture of 10W40 oil+10% water. Curve 304 corresponds to the case where the liquid consisted of old engine oil. Curve 305 corresponds to the case where the liquid consisted of IPA (isopropanol alcohol) cleaner. Curve 306 corresponds to the case where the liquid consisted of a 50/50 mixture of IPA cleaner and water. Curve 307 corresponds to the case where the liquid consisted of relatively hard water.

The six curves shown in FIG. 12 illustrate respectively how the resistance (and thus temperature) of the resistive element 50 changed as a function of time during application of the heating pulse when the resistive element 50 was in contact with each of six different formulations of liquid based on diesel fuel. Curve 401 corresponds to the case where the liquid consisted of diesel fuel only. Curve 402 corresponds to the case where the liquid consisted of diesel fuel with 1% water. Curve 403 corresponds to the case where the liquid consisted of diesel fuel with 2% water. Curve 404 corresponds to the case where the liquid consisted of diesel fuel with 5% water. Curve 405 corresponds to the case where the liquid consisted of diesel fuel with 10% water. Curve 406 corresponds to the case where the liquid consisted of a highly impure "sludge" composition.

In the curves of FIGS. 11 and 12 it can clearly be seen that changes in the composition of the liquids involved led to marked changes not only in the absolute values of resistance of the resistive element 50 at particular points in time, but also in the way the resistances varied as a function of time (i.e. the shapes of the curves). Either or both of the absolute values and shapes of the curves may therefore be used to detect changes in composition of the liquid. The shapes of the curves may be parameterised for example by looking at derivatives of the resistivity (or temperature) with respect to time (e.g. first derivative, second derivative, etc.). A change in the composition of the liquid may be detected by looking for a change in a derivative of the resistivity that is greater than a predetermined threshold for example. As mentioned earlier, the nature of the input pulse may also be varied to optimise sensitivity (thereby changing for example the amount of energy input, the rate of energy input, the rate of change of energy input, etc.).

The curves in FIGS. 11 and 12 also illustrate how phase changes of components of the liquid (e.g. vaporisation of water) lead to distinct (and therefore detectable) features in the curves. For example, in the experimental setup of FIGS. 11 and 12, an 80 deg C. temperature rise (which is approximately what would be required to reach the boiling point of water) results in a 23% change in the resistivity of the resistive element 50. When converted to voltage units this is 2.05 Volts. The simplest effects of the vaporisation of water can be seen in the curves 301 and 307 in FIG. 11, representing respectively relatively soft and relatively hard water with no significant other components. When the temperature reaches around 100 deg C. (an increase in voltage of about 2.05 Volts), it can be seen that the respective curves start to become unstable, exhibiting a sequence of falls and rises in temperature. The falls occur when pockets of vapour are created and then subsequently filled will cooler water (which leads to the fall in temperature). The water is then heated again (which leads to a rise in temperature) until the next pocket of vapour is created. Identification of such behaviour can be used to identify the boiling points of the liquid (or components within the liquid), thereby providing information about the composition of the liquid or of components within the liquid.

In curves 402-406 in FIG. 12, it can be seen that the presence of water greatly affects how efficiently heat is carried away from the resistive element 50 relative to the case where the diesel is relatively uncontaminated (curve 401). It is noted here that the first 100 deg C. corresponds to a rise in the output voltage of 2.05 Volts and each subsequent 100 deg C. corresponds to a rise in the output voltage of 2.73 Volts. Thus, it will be seen that the temperature rises up to around 350 deg C. in this example testing of the diesel fuel. The slight change in slope seen in curve 401 at about 14 ms is because the relatively pure diesel actually still comprises trace amounts of water (estimated to be of the order of 0.1%). The fact that even trace amounts of water have such a large effect on the heat transfer characteristics of the water emphasises the sensitivity of this approach to detecting contamination.

The shapes of the curves for mixtures of oil and water shown in FIG. 11 and the curves for mixtures of diesel fuel and water shown in FIG. 12 are very different. This is likely due to the different relative miscibilities of the components involved in each case and other factors which affect the properties of the resulting two-phase mixtures.

Figure 8:
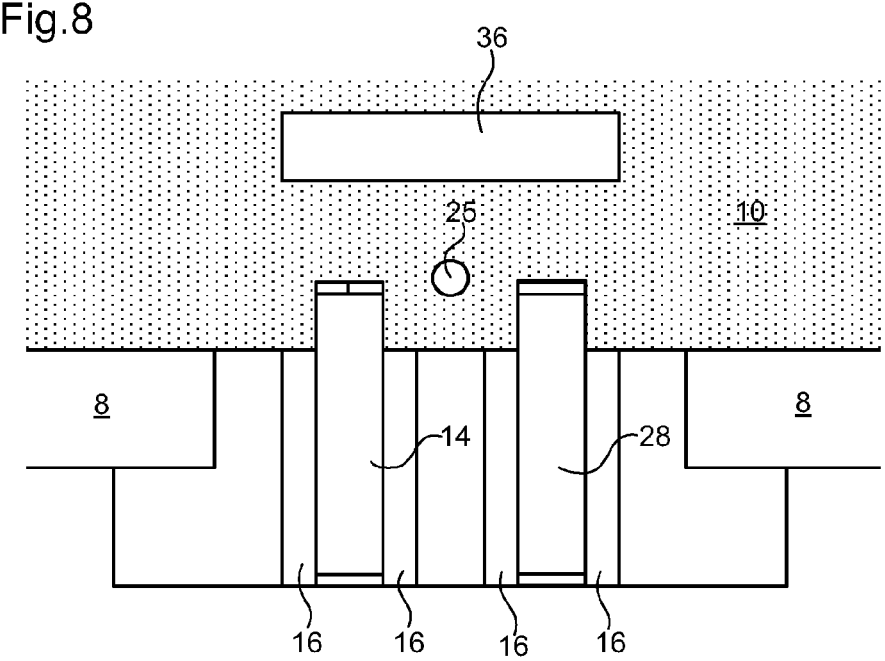
FIG. 8 is a schematic side sectional view of the type shown in FIG. 4 in an embodiment further comprising a single-coil eddy current sensor.
Figure 9:
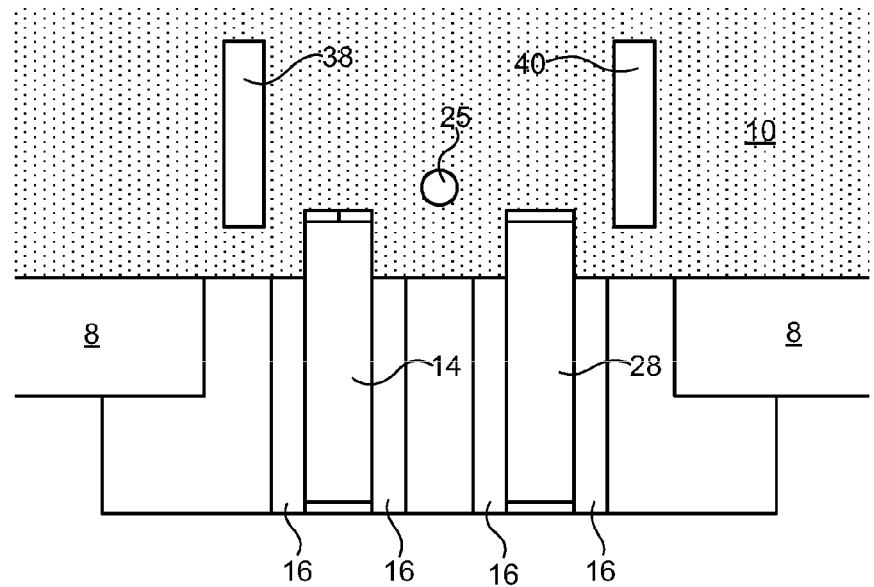
FIG. 9 is a schematic side sectional view of the type shown FIG. 4 in an embodiment further comprising a two-coil eddy current sensor.

In an embodiment, the apparatus 2 further comprises an eddy current sensor 36 configured to detect metallic contaminants in the liquid. Example configurations are shown schematically in FIGS. 8 and 9 in the context of an arrangement of the type shown in FIG. 4. However, many other configurations for the eddy current sensor 36 can be envisaged and can be used in combination with any embodiment of the invention. The eddy current sensor may comprise one coil (as in FIG. 8) or two coils (as in FIG. 9) or more coils. The coils may be configured to detect the presence of metallic impurities preferentially in a portion of the liquid 10 that is adjacent to the first and/or second surfaces 31,32 and/or the resistive element 50. The eddy current sensor 36 can provide further information about the level of contamination and/or the type of contamination of the liquid.

Embodiments of the invention can be applied to detect contamination of liquids in a wide variety of contexts. For example the liquid can be lubricating or cooling liquid in any machine having moving parts, including an engine and a gearbox. The liquid may comprise hydraulic liquid or fuel. The liquid can also be a cleaning liquid, for example a cleaning liquid using a food manufacturing facility.

Figure 19:
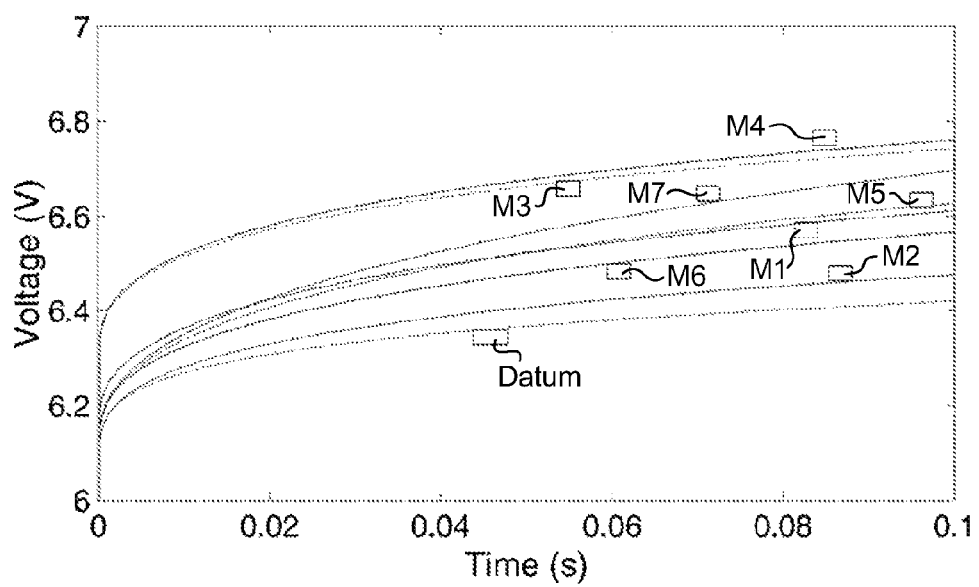
FIG. 19 is a graph showing changes of resistance with time during heating of a resistive element in contact with different solid samples.

FIG. 19 show representative data showing the result of applying a heating pulse to a resistive element 50 of the type discussed above with reference to FIG. 5 or any of FIGS. 13-18 when the sample comprises a variety of different solid objects. The resistive element 50 was encapsulated in a support material comprising a thin electrically conductive film. The curve for a reference solid object is labelled "Datum". Curves for other solid objects of nominally identical composition are marked M1-M7. In this particular example the solid objects are samples of fine grained rock. The vertical axis shows an output voltage from the resistive element 50 during application of the heating pulse. The vertical axis is proportional to the resistance of the resistive element 50, which in turn varies in a predetermined way as a function of the temperature of the resistive element 50. The horizontal axis measures a time interval spanning application of the heating pulse. FIG. 19 demonstrates that even for solid samples of nominally identical composition, small changes in actual composition lead to detectable differences in the response of the resistive element 50 to a heating pulse, thereby enabling detection of deviations of the samples from a reference ("Datum").

In embodiments where the resistive element 50 is separated from the sample 82 by a support material or other material, the electrical current should be applied for a period (e.g. pulse length) which is long enough for the heat generated to pass significantly into the sample 82. If the pulse length is too short the heating will only sample the support material or other material and provide information about the thermal properties of the support material or other material, which may not be of interest. This is why the pulse length (0.1 s) in the example of FIG. 19 (where the resistive element is encapsulated by a support material) is much longer than the pulse lengths used in the examples of FIGS. 10-12. The fact that the heat generated at the resistive element 50 samples different layers sequentially can be used to obtain information about different layers of a sample in a single measurement. Variation of the resistance of the resistive element in different time windows can be attributed to different layers (earlier time windows corresponding to shallower layers than deeper time windows). This provides a convenient way of obtaining information about the thermal properties of a sample selectively at different depths within the sample.

The invention claimed is:

1. An apparatus for detecting a composition of a sample, comprising:
   a first probe element configured to provide a first surface in direct contact with the sample, and a second surface that is not in direct contact with the sample;
   a measurement system configured to measure a rate of heat transfer through the first surface; and
   a processing unit configured to analyse the measured rate of heat transfer in order to detect a heat transfer characteristic of the sample that is indicative of the composition of the sample.

2. The apparatus of claim 1, wherein:
   the sample is a liquid and the detecting of the composition of the sample comprises detecting contamination of the liquid;
   the first probe element is configured to provide the first surface in direct contact with the liquid, and the second surface not in direct contact with the liquid; and
   the processing unit is configured to analyse the measured rate of heat transfer in order to detect a change in a heat transfer characteristic of the liquid that is indicative of contamination of the liquid.

3. The apparatus of claim 1, wherein the first probe element penetrates through a containing wall containing the sample.

4. The apparatus of claim 1, further comprising a first-probe-element heater configured to heat the first probe element.

5. The apparatus of claim 1, further comprising an eddy current sensor configured to detect metallic contaminants in a liquid.

6. The apparatus of claim 1, wherein:
   the sample is a liquid and the detecting of the composition of the sample comprises detecting contamination of the liquid; and
   the processing unit is configured to output a signal indicating detection of contamination of the liquid when a change in the heat transfer characteristic of the liquid that is indicative of contamination is detected.

7. The apparatus of claim 1, wherein the apparatus comprises a resistive element configured to act as a first-probe-element heater to heat the first probe element, and a first surface temperature sensor to measure a first temperature at the first surface.

8. The apparatus of claim 7, wherein the resistive element comprises a thin film resistive element.

9. The apparatus of claim 1, wherein the measurement system comprises:
a first surface temperature sensor configured to measure a first temperature at the first surface; and
a second surface temperature sensor configured to measure a second temperature at the second surface, wherein
the measurement system is configured to use the measured first and second temperatures to measure the rate of heat transfer through the first surface.

10. The apparatus of claim 9, wherein:
the measurement system is further configured to receive input from a sample temperature sensor configured to measure a temperature of the sample; and
the processing unit is configured to use the measurement of the temperature of the sample when detecting the change in the heat transfer characteristic of the sample.

11. The apparatus of claim 9, further comprising a second probe element configured to provide a third surface in direct contact with the sample, and a fourth surface that is not in direct contact with the sample, wherein
the measurement system is configured to measure the rate of heat transfer through the third surface; and
the processing unit is configured to analyse the measured rates of heat transfer through the first and third surfaces in order to detect the heat transfer characteristic of the sample that is indicative of the composition of the sample or, where the sample is a liquid, the change in the heat transfer characteristic of the liquid that is indicative of contamination of the liquid.

12. The apparatus of claim 11, wherein
the measurement system further comprises:
a third surface temperature sensor configured to measure a third temperature of the third surface; and
a fourth surface temperature sensor configured to measure a fourth temperature of the fourth surface, wherein
the measurement system is configured to use the measured third and fourth temperatures to measure the rate of heat transfer through the third surface.

13. The apparatus of claim 11, wherein the second probe element penetrates through a containing wall containing the sample.

14. The apparatus of claim 11, further comprising a magnet configured to attract magnetic or magnetisable particles preferentially to a region adjacent to a selected one of the first surface and the third surface.

15. The apparatus of claim 11, wherein:
the first and third surfaces have the same size and shape; and
the first and second probe elements are configured such that, in use, when a temperature of the sample adjacent to the first and third surfaces is the same, the rate of heat transfer into the first surface is different from the rate of heat transfer into the third surface.

16. The apparatus of claim 15, wherein the first probe element is formed from a first material, the second probe element is formed from a second material, and the first and second materials have different thermal conductivities, such that, in use, when the temperature of the sample adjacent to the first and third surfaces is the same, the rate of heat transfer into the first surface is different from the rate of heat transfer into the third surface.

17. An engine or gearbox comprising a sump for containing a lubricating oil, wherein the engine or gearbox comprises the apparatus of claim 1, wherein said sample comprises the lubricating oil.

18. A fuel container for storing a fuel, comprising the apparatus of claim 1, wherein said sample comprises the fuel.

19. A method of detecting a composition of a sample, comprising:
providing a first probe element having a first surface in direct contact with the sample, and a second surface that is not in direct contact with the sample;
measuring a rate of heat transfer through the first surface; and
analysing the measured rate of heat transfer in order to detect a heat transfer characteristic of the sample that is indicative of the composition of the sample.

20. The method of claim 19, wherein:
the sample is a liquid and the detecting of the composition of the sample comprises detecting contamination of the liquid;
the first surface is in direct contact with the liquid, and the second surface is not in direct contact with the liquid;
the analysing comprises analysing the measured rate of heat transfer in order to detect a change in a heat transfer characteristic of the liquid that is indicative of contamination of the liquid;
the rate of heat transfer through the first surface is measured at a temperature at the first surface that is below the boiling point of a predetermined contaminant and at a temperature at the first surface that is above the boiling point of the predetermined contaminant; and
the detection of a change in the heat transfer characteristic comprises comparing the measured rate of heat transfer at the temperature at the first surface that is below the boiling point of the predetermined contaminant with the measured rate of heat transfer at the temperature at the first surface that is above the boiling point of the predetermined contaminant.

* * * * *